US010610279B2

(12) United States Patent
Burnett et al.

(10) Patent No.: US 10,610,279 B2
(45) Date of Patent: Apr. 7, 2020

(54) APPARATUS AND METHODS FOR REGULATING CRYOGENIC TREATMENT

(71) Applicant: Channel Medsystems, Inc., San Francisco, CA (US)

(72) Inventors: Daniel R. Burnett, San Francisco, CA (US); Ric Cote, Oakland, CA (US); William W. Malecki, Piedmont, CA (US); Brian M. Neil, San Francisco, CA (US); David Beaulieu, El Cerrito, CA (US); Benjamin D. Voiles, San Francisco, CA (US); Vincent Lopresti, San Francisco, CA (US)

(73) Assignee: Channel Medsystems, Inc., Emeryville, CA (US)

( * ) Notice: Subject to any disclaimer, the term of this patent is extended or adjusted under 35 U.S.C. 154(b) by 454 days.

(21) Appl. No.: 14/265,799

(22) Filed: Apr. 30, 2014

(65) Prior Publication Data
US 2015/0289920 A1 Oct. 15, 2015

Related U.S. Application Data

(60) Provisional application No. 61/977,773, filed on Apr. 10, 2014.

(51) Int. Cl.
*A61B 18/02* (2006.01)
*A61B 18/00* (2006.01)

(52) U.S. Cl.
CPC ...... *A61B 18/02* (2013.01); *A61B 2018/0022* (2013.01); *A61B 2018/00041* (2013.01);
(Continued)

(58) Field of Classification Search
CPC ............ A61B 18/02; A61B 2018/0022; A61B 2018/00041; A61B 2018/00559; F16K 17/168
See application file for complete search history.

(56) References Cited

U.S. PATENT DOCUMENTS 2,849,002 A 8/1958 Oddo
3,343,544 A 9/1967 Dunn et al.
(Continued)

FOREIGN PATENT DOCUMENTS

GB 2026324 2/1980
GB 2094636 9/1982
(Continued)

*Primary Examiner* — Michael F Peffley
*Assistant Examiner* — Bo Ouyang
(74) *Attorney, Agent, or Firm* — Levine Bagade Han LLP

(57) ABSTRACT

Apparatus and methods for regulating cryogenic treatments are disclosed which comprise devices and methods for delivering controlled treatment of a cryoablative agent. In one variation, such devices may generally comprise an elongate probe having a distal tip and a flexible length, at least one infusion lumen positioned through or along the elongate probe, wherein the infusion lumen defines one or more openings along its length, and a liner expandably enclosing the probe. An inflow reservoir or canister valve may be fluidly coupled with a reservoir or canister containing the cryoablative agent and a modulation control unit may also be fluidly coupled with the inflow reservoir or canister valve and in fluid communication with the at least one infusion lumen. Additionally, a warming element may also be thermally coupled with the reservoir or canister.

20 Claims, 23 Drawing Sheets

(52) U.S. Cl.
CPC ........... *A61B 2018/00559* (2013.01); *A61B 2018/00577* (2013.01); *A61B 2018/00744* (2013.01); *A61B 2018/00791* (2013.01); *A61B 2018/0268* (2013.01)

(56) References Cited

U.S. PATENT DOCUMENTS

| | | |
|---|---|---|
| 3,398,738 A | 8/1968 | Lamb et al. |
| 3,696,813 A | 10/1972 | Wallach |
| 3,924,628 A | 12/1975 | Droegemueller |
| 4,072,152 A | 2/1978 | Linehan |
| 4,275,734 A | 6/1981 | Mitchiner |
| 4,457,334 A * | 7/1984 | Becker ............... F16K 17/168 137/461 |
| 4,949,718 A | 8/1990 | Neuwirth |
| 4,968,316 A * | 11/1990 | Hergenroeder .... A61B 17/6425 606/57 |
| 5,084,044 A | 1/1992 | Quint |
| 5,228,441 A | 7/1993 | Lundquist |
| 5,281,215 A | 1/1994 | Milder |
| 5,334,181 A | 8/1994 | Rubinsky et al. |
| 5,370,134 A | 12/1994 | Chin et al. |
| 5,382,252 A | 1/1995 | Failla |
| 5,437,665 A | 8/1995 | Munro |
| 5,458,597 A | 10/1995 | Edwards et al. |
| 5,501,681 A | 3/1996 | Neuwirth et al. |
| 5,769,880 A | 6/1998 | Truckai et al. |
| 5,776,129 A | 7/1998 | Mersch |
| 5,800,493 A | 9/1998 | Stevens et al. |
| 5,827,269 A | 10/1998 | Saadat |
| 5,868,735 A | 2/1999 | Lafontaine |
| 5,879,347 A | 3/1999 | Saadat |
| 5,902,299 A | 5/1999 | Jayaraman |
| 5,916,212 A | 6/1999 | Baust et al. |
| 5,921,982 A | 7/1999 | Lesh et al. |
| 5,954,714 A | 9/1999 | Saadat |
| 5,957,962 A | 9/1999 | Wallsten et al. |
| 6,057,689 A | 5/2000 | Saadat |
| 6,066,132 A | 5/2000 | Chen et al. |
| 6,141,985 A | 11/2000 | Cluzeau et al. |
| 6,159,160 A | 12/2000 | Hsei et al. |
| 6,235,019 B1 | 5/2001 | Lehmann et al. |
| 6,241,722 B1 | 6/2001 | Dobak et al. |
| 6,270,476 B1 | 8/2001 | Santoianni et al. |
| 6,270,493 B1 | 8/2001 | Lalonde et al. |
| 6,280,439 B1 | 8/2001 | Martin et al. |
| 6,283,959 B1 | 9/2001 | Lalonde et al. |
| 6,290,696 B1 | 9/2001 | Lafontaine |
| 6,355,029 B1 | 3/2002 | Joye et al. |
| 6,497,703 B1 | 12/2002 | Korteling et al. |
| 6,517,533 B1 | 2/2003 | Swaminathan |
| 6,530,234 B1 | 3/2003 | Dobak, III et al. |
| 6,547,784 B1 | 4/2003 | Thompson |
| 6,554,780 B1 | 4/2003 | Sampson et al. |
| 6,569,158 B1 | 5/2003 | Abboud et al. |
| 6,575,932 B1 | 6/2003 | O'Brien et al. |
| 6,575,933 B1 | 6/2003 | Wittenberger et al. |
| 6,589,234 B2 | 7/2003 | Lalonde et al. |
| 6,595,988 B2 | 7/2003 | Wittenberger et al. |
| 6,602,247 B2 | 8/2003 | Lalonde |
| 6,607,545 B2 | 8/2003 | Kammerer et al. |
| 6,648,878 B2 | 11/2003 | Lafontaine |
| 6,648,879 B2 | 11/2003 | Joye et al. |
| 6,743,184 B2 | 6/2004 | Sampson et al. |
| 6,752,802 B1 | 6/2004 | Isenberg |
| 6,758,831 B2 | 7/2004 | Ryan |
| 6,786,901 B2 | 9/2004 | Joye et al. |
| 6,872,183 B2 | 3/2005 | Sampson et al. |
| 6,875,209 B2 | 4/2005 | Zvuloni et al. |
| 6,951,569 B2 | 10/2005 | Nohilly |
| 6,989,009 B2 | 1/2006 | Lafontaine |
| 7,022,120 B2 | 4/2006 | Lafontaine |
| 7,063,670 B2 | 6/2006 | Sampson et al. |
| 7,101,367 B2 | 9/2006 | Xiao et al. |
| 7,195,625 B2 | 3/2007 | Lentz |
| 7,281,550 B2 | 10/2007 | Ziegler |
| 7,306,589 B2 | 12/2007 | Swanson |
| 7,381,208 B2 | 6/2008 | van der Walt et al. |
| 7,500,973 B2 | 3/2009 | Vancelette et al. |
| 7,566,341 B2 | 7/2009 | Keller et al. |
| 7,727,228 B2 | 6/2010 | Abboud |
| 7,785,289 B2 | 8/2010 | Rios et al. |
| 7,794,454 B2 | 9/2010 | Abboud et al. |
| 7,850,681 B2 | 12/2010 | LaFontaine |
| 8,088,125 B2 | 1/2012 | Lafontaine |
| 8,206,345 B2 | 6/2012 | Abboud et al. |
| 8,225,643 B2 | 7/2012 | Abboud et al. |
| 8,382,747 B2 | 2/2013 | Abboud et al. |
| 8,439,906 B2 | 5/2013 | Watson |
| 8,545,491 B2 | 10/2013 | Abboud et al. |
| 8,579,890 B2 | 11/2013 | Hon |
| 8,663,211 B2 | 3/2014 | Fourkas et al. |
| 8,715,274 B2 | 5/2014 | Watson |
| 8,911,434 B2 | 12/2014 | Wittenberger |
| 9,027,389 B2 | 5/2015 | Abboud et al. |
| 2002/0082635 A1 | 6/2002 | Kammerer et al. |
| 2002/0099364 A1 | 7/2002 | Lalonde |
| 2003/0060762 A1 | 3/2003 | Zvuloni et al. |
| 2003/0153940 A1 | 8/2003 | Nohilly et al. |
| 2004/0034344 A1 | 2/2004 | Ryba |
| 2004/0167505 A1 | 8/2004 | Joye et al. |
| 2004/0181136 A1 | 9/2004 | McDaniel et al. |
| 2005/0081541 A1 | 4/2005 | Copping |
| 2005/0107855 A1 | 5/2005 | Lennox et al. |
| 2005/0177147 A1 | 8/2005 | Vancelette et al. |
| 2005/0177148 A1 | 8/2005 | van der Walt et al. |
| 2005/0182394 A1 * | 8/2005 | Spero ............... A61B 10/0266 606/21 |
| 2005/0215989 A1 | 9/2005 | Abboud et al. |
| 2006/0259023 A1 | 11/2006 | Abboud et al. |
| 2007/0088247 A1 | 4/2007 | Bliweis et al. |
| 2007/0203396 A1 | 8/2007 | McCutcheon et al. |
| 2007/0237739 A1 | 10/2007 | Doty |
| 2008/0255552 A1 * | 10/2008 | DeLonzor ............... A61B 18/02 606/23 |
| 2008/0294154 A1 | 11/2008 | Ibrahim et al. |
| 2009/0076573 A1 | 3/2009 | Burnett et al. |
| 2009/0138000 A1 | 5/2009 | Vancelette et al. |
| 2009/0163902 A1 | 6/2009 | DeLonzor et al. |
| 2009/0299355 A1 | 12/2009 | Bencini et al. |
| 2009/0299356 A1 | 12/2009 | Watson |
| 2009/0306588 A1 | 12/2009 | Nguyen et al. |
| 2010/0004595 A1 | 1/2010 | Nguyen et al. |
| 2010/0049190 A1 | 2/2010 | Long et al. |
| 2010/0125266 A1 | 5/2010 | Deem et al. |
| 2011/0082453 A1 | 4/2011 | Fischer et al. |
| 2011/0106130 A1 * | 5/2011 | Rajkovic ............... A61M 29/02 606/193 |
| 2011/0152722 A1 | 6/2011 | Yackel |
| 2012/0089047 A1 * | 4/2012 | Ryba ............... A61B 18/02 600/554 |
| 2012/0101485 A1 | 4/2012 | Wittenberger |
| 2012/0197245 A1 * | 8/2012 | Burnett ............... A61B 18/02 606/21 |
| 2012/0253336 A1 | 10/2012 | Littrup et al. |
| 2013/0041358 A1 | 2/2013 | Babkin et al. |
| 2013/0190744 A1 * | 7/2013 | Avram ............... A61F 7/10 606/21 |
| 2013/0274792 A1 * | 10/2013 | Dehara ............... A61B 17/12113 606/200 |
| 2014/0012156 A1 | 1/2014 | Burnett et al. |

FOREIGN PATENT DOCUMENTS

| | | |
|---|---|---|
| JP | 5-168646 | 7/1993 |
| WO | WO 1998/029068 | 7/1998 |
| WO | WO 2002/051491 | 7/2002 |
| WO | WO 2010/135602 | 11/2010 |
| WO | WO 2012/106260 | 8/2012 |
| WO | WO 2013/067421 | 5/2013 |

* cited by examiner

APPARATUS AND METHODS FOR REGULATING CRYOGENIC TREATMENT

CROSS-REFERENCE TO RELATED APPLICATIONS

This application claims the benefit of priority to U.S. Prov. App. 61/977,773 filed Apr. 10, 2014, which is incorporated herein by reference in its entirety.

FIELD OF THE INVENTION

The present invention relates to medical devices. In particular, the present invention relates to methods and apparatus for regulating the cryoablative treatment of tissue regions.

BACKGROUND OF THE INVENTION

In the last few decades, therapeutic intervention within a body cavity or lumen has developed rapidly with respect to delivery of energy via radiofrequency ablation. While successful in several arenas, radiofrequency ablation has several major downsides, including incomplete ablation, frequent lack of visualization during catheter insertion, potential for overlap during treatment (with some areas receiving twice as much energy as other areas), charring of tissues and requirements for frequent debridement, frequent requirements for additional doses of energy after debridement, and potential perforation of the body cavity or lumen due to the rigidity of the RF electrodes.

The current state of the art would benefit from minimally invasive devices and methods which deliver thermal energy to a desired area or extract energy from a desired area, in a consistent, controlled manner that does not char or inadvertently freeze certain tissues or create excessive risk of unwanted organ or lumen damage.

SUMMARY OF THE INVENTION

Generally, devices for delivering controlled treatment may comprise an elongate probe having a distal tip and a flexible length, at least one infusion lumen positioned through or along the elongate probe, wherein the infusion lumen defines one or more openings along its length, a liner expandably enclosing the probe, an inflow reservoir or canister valve fluidly coupled with a reservoir or canister containing a cryoablative agent, a modulation control unit fluid coupled with the inflow reservoir or canister valve and in fluid communication with the at least one infusion lumen, and a warming element thermally coupled with the reservoir or canister.

One method for utilizing the treatment assembly for cryoablatively treating tissue, e.g., uterine tissue, may generally comprising monitoring a temperature or pressure of the reservoir or canister containing a cryoablative agent, maintaining the temperature of the reservoir or canister at a predetermined level, positioning an elongate probe into a body lumen to be treated, expanding a liner enclosing the probe into contact against the body lumen, and infusing a cryoablative agent through a delivery lumen such that the cryoablative agent passes into an infusion lumen, through one or more unobstructed openings, and into contact against an interior of the liner.

In controlling or modulating the flow of the cryoablative agent, the inflow reservoir or canister valve which is fluidly coupled with the reservoir or canister may be utilized. Such a valve may generally comprising a valve body, a reservoir interface extending from the valve body and configured for fluidly coupling with the reservoir or canister containing the cryoablative agent, a modulation control interface defined along the body and configured for fluidly coupling to a modulation control interface, a valve stem seated within a valve stem channel defined within the valve body, an inflow lumen defined through the valve body and extending between the reservoir interface and the modulation control interface, where the valve stem is movable between a first position which obstructs the inflow lumen and a second position which opens the inflow lumen, a venting lumen defined through the valve body and extending between the reservoir interface and a vent opening, and a vent piston which is movable between a first position which obstructs the venting lumen and a second position which opens the venting lumen. Alternatively, the valve stem may be configured to include three positions including a first position which obstructs the inflow lumen, a second position which opens the inflow lumen, and a third optional position which opens the venting lumen.

To facilitate the liner expanding and conforming readily against the tissue walls of the uterus, the liner may be inflated with a gas or liquid. Once the elongate shaft has been introduced through the cervix and into the uterus, the distal opening of the shaft may be positioned distal to the internal os and the liner may be deployed either from within the shaft or from an external sheath. The liner may be deployed and allowed to unfurl or unwrap within the uterus. The cooling probe may be introduced through the shaft and into the liner interior. As the cryoablative agent (e.g., cryoablative fluid) is introduced into and distributed throughout the liner interior, the exhaust catheter may also define one or more openings to allow for the cryoablative fluid to vent or exhaust from the interior of the liner.

A coolant reservoir, e.g., nitrous oxide canister, may be fluidly coupled to the handle and/or elongate shaft via a coolant valve which may be optionally controlled by the microcontroller. The coolant reservoir may be in fluid communication with the cooling probe assembly and with the interior of the balloon. Additionally, an exhaust lumen in communication with the elongate probe and having a back pressure valve may also include a pressure sensor where one or both of the back pressure sensor and/or valve may also be in communication with the microcontroller.

Yet another variation of the treatment assembly may incorporate a housing having a handle and a reservoir housing extending from and attached directly to the handle. The sheath having the liner may extend from the housing while an actuator may be located, for instance, along the handle to enable the operator to initiate the cryoablative treatment. A reservoir or canister fully containing the cryoablative fluid may be inserted and retained within the reservoir housing. The reservoir housing and/or the handle may further incorporate a reservoir engagement control which may be actuated, e.g., by rotating the control relative to the handle, to initially open fluid communication with the reservoir or canister to charge the system for treatment.

The reservoir or canister may be inserted into the reservoir housing and into secure engagement with a reservoir or canister valve which may be coupled to the reservoir engagement control. The valve may be adjusted to open the reservoir or canister for treatment or for venting of the discharged cryoablative fluid during or after treatment. An inflow modulation control unit (e.g., an actuatable solenoid mechanism) may be coupled directly to the reservoir or canister valve and the cryoablative fluid line may be coupled directly to the modulation control unit and through the sheath and into fluid communication within the liner.

The modulation control unit 96 may be in electrical communication with the microprocessor or controller via an electrical line. The inflow of the cryoablative fluid contained within the reservoir or canister may flow through an inflow line within the canister and through the reservoir or canister valve and modulation control unit and into cryoablative fluid line for introduction within the liner via infusion line. One or more pressure measurement lines which are in fluid communication with the interior of the liner may extend through the sheath and in communication with corresponding pressure sensors which in turn are in electrical communication with microprocessor or controller via electrical lines. The pressure sensed by the measurement lines may be due (at least in part) to the expansion of the cryoablative fluid (e.g., nitrous oxide) which contacts the interior walls of the liner. Hence, microprocessor or controller may actively control the modulation control unit in a corresponding manner based on the detected pressure values within the liner sensed via pressure sensors.

To maximize patient comfort, the liner may be initially inflated with air to about, e.g., 140 mmHg, prior to the infusion of the cryoablative fluid. However, once the cryoablative fluid is introduced into the liner, the transition from air to the cryoablative fluid may create a brief fluctuation in the intracavitary pressure, e.g., spike or dip in the pressure. For instance, the pressure with which the cryoablative fluid is introduced may initially be relatively higher, e.g., about 140 mmHg. Over the course of the treatment procedure, e.g., 150 second, the pressure within the liner may result in a relatively lower pressure, e.g., about 95 mmHg.

Hence, the internal pressure within the liner during treatment may be controlled by the microprocessor or controller which may modulate the reservoir or canister valve via the modulation control unit (e.g., a solenoid valve or other mechanism) in response to the intracavitary pressures sensed by the pressure sensors. This closed-loop system may incorporate, for instance, dual pressure measuring tubes and corresponding sensors as both a redundant safety system and to also identify possible erroneous data points. The closed-loop control system can be controlled by a PID or non-PID software algorithm via the microprocessor or controller. Additionally, the modulation control unit may be used controlled by the microprocessor or controller to control the flow rate of the cryoablative fluid during the treatment procedure to optimize ablation depth and minimize the amount of cryoablative fluid needed.

During or after the treatment procedure, the discharged cryoablative fluid evacuated from the interior of the liner passes through the exhaust line which may run through the handle and reservoir housing. Hence, a system for ensuring that the discharged cryoablative fluid passing through the exhaust line is fully evaporated can be incorporated into the treatment assembly. A liquid exhaust trap which also functions as a heatsink for converting any present liquid cryogen into a gas may be integrated, for instance, directly into the reservoir housing or handle. Because the liquid exhaust trap functions as a heatsink, the trap may be fabricated from a thermally conductive material which also has a relatively large heat capacity, e.g., aluminum, copper, or other metals. In other variations, plastics such as polycarbonate (which generally have heat capacities greater than metals such as aluminum but relatively lower thermal conductivity values) may also be utilized for fabricating the liquid exhaust trap. During use, as the discharged cryoablative fluid from the liner passes through the exhaust line and into the fluid trap portion of liquid exhaust trap, any liquid form of the cryoablative fluid may collect within the fluid trap while the gaseous form may continue to be vented through the exhaust lumen and out through the evacuating exhaust line. The captured liquid may be subsequently warmed enough by contact with the liquid exhaust trap to turn into a gaseous form for venting through the exhaust line.

With the discharged cryoablative fluid in a completely gaseous state, the evacuating exhaust line may be vented to the surrounding environment or optionally coupled to a scavenging system to collect the discharged gas to limit exposure. Such scavenging collection systems may incorporate features such as orifices or valves to prevent any vacuum applied by the scavenging unit from interfering with the backpressure within the treatment device.

In further controlling the flow of the cryoablative fluid within the treatment assembly, the reservoir or canister valve which is coupled directly to the reservoir or canister may also incorporate a number of flow control features. One variation of the reservoir or canister valve may include an integrated reservoir lumen insert extending from the reservoir interface for direct insertion into the reservoir or canister to facilitate the transfer of the cryoablative fluid through the valve and into the treatment assembly. A reservoir seal may be incorporated to ensure a fluid tight seal between the reservoir or canister and the reservoir interface. The valve may include a valve body which defined pathways for normal fluid flow as well as a venting pathway for emptying of the reservoir or canister.

The valve body may have the reservoir interface extending from the body for secure engagement with the reservoir or canister (e.g., via a threaded engagement). The valve body may further include a modulation control interface which defines an interface seal for securely coupling (e.g., via a threaded engagement) with a modulation control interface extending from the inflow modulation control unit. A valve stem may be seated within a valve stem channel defined within the valve body. The valve stem may be secured to the valve body via a threaded engagement and a valve stem seal which ensures a fluid-tight connection between the two components. The valve stem may be attached to a valve stem coupler which is connected to the reservoir engagement control via a control member.

During use, the reservoir engagement control may be rotated (e.g., about 45 degrees) about the reservoir housing and/or the handle. This in turn may rotate the control member and valve stem coupler which further rotates the valve stem relative to the valve body and opens the valve stem seal. The opened valve stem seal then enables the flow of the cryoablative fluid into the reservoir lumen insert and into the proximal inflow lumen located proximal to the valve stem, past the opened valve stem, and into the distal inflow lumen for further passage into the inflow modulation control unit.

Actuation of the reservoir engagement control, control member, and/or valve stem coupler may optionally send an electrical signal to the microprocessor or controller that the treatment assembly is charged with the cryoablative fluid and ready for a treatment procedure. Once the treatment procedure is completed and the inflow modulation control unit has been optionally closed to any further inflow of the cryoablative fluid, a vent pin may be actuated or pulled relative to the valve body to release a vent piston. With the vent pin secured in the valve body, the vent piston may seal a venting lumen but with the vent pin removed, the vent piston may freely translate relative to the valve body thus allowing any remaining cryoablative fluid within the reservoir or canister to vent through the venting lumen (with the valve stem still in its open position) and into the environment or into a collection reservoir, as described herein.

Yet another feature which may be optionally incorporated into the treatment assembly for controlling or modulating the flow of the cryoablative fluid may include an actuatable dome-shaped valve located within the exhaust block at a proximal end of the sheath. Although shown and described as a dome-shaped valve, such a valve is one of a variety of pneumatic and/or electro-mechanical valves that may be used to open and close the exhaust gas pathway in the assembly described herein. The exhaust block may comprise in part a body which defines an exhaust lumen in fluid communication with the interior of the liner. The exhaust lumen may also be in fluid communication with a pump/vacuum lumen which provides a channel for air for the initial inflation of the liner against the tissue surface prior to infusion of the cryoablative fluid.

The valve may generally comprise a dome-shaped flexible member attached at its periphery to the body via attachment. The flexible member may further include a seal which extends from a central portion of the concave surface of the flexible member. The flexible member may be located within a pressurization chamber which normally exerts a pressure which is less than a deflection force required to collapse the flexible member. When the treatment assembly is used to initially puff the liner with air to force the liner into contact with the surrounding tissue, the air may pass through the pump/vacuum lumen and into the interior of the liner. The air within the pressurization chamber may also be pressurized by the same pump such that the pressure increase collapses the flexible member and forces the seal into contact against a corresponding sealing lip located at an opening of the exhaust lumen adjacent to the seal.

When the initial pressurization of the liner has been completed, the air may bleed out of the lumens as well out of the pressurization chamber allowing the flexible member to reconfigure into its opened domed shape and to release the seal from the sealing lip. This may then allow for the exhaust from the liner interior to flow through the exhaust lumen, through an exhaust chamber, and further into an exhaust lumen for venting from the treatment assembly.

In further facilitating a treatment procedure, the liner may also be configured to aid in its removal from the underlying tissue after a cryoablation treatment. After the tissue has been treated, the liner may remain frozen on the underlying uterine tissue preventing removal of the liner from the patient's body for up to several minutes. The liner may be left in the patient for a period of time after the cryoablation treatment until the tissue thaws as pulling the liner from the tissue prematurely may tear the liner; however, leaving the liner in place may increase patient discomfort. Hence, to facilitate removal of the liner from the underlying frozen tissue, a number of different warming techniques may be optionally implemented.

Circulating a warm or room temperature fluid within the liner is one method for thawing the liner and adjacent tissue to expedite the removal of the liner. A gas (e.g., air, expanded helium, etc.) may be used instead of a liquid as a warming gas may prevent the creation of a solid which could potentially block the exhaust gas pathway. Additionally, use of a warming gas may also slow the boiling-off of any remaining cryoablative fluid as boiling-off the cryoablative fluid too quickly could create a pressure spike within the liner. A liquid with a freezing point lower than the boiling point of the cryoablative fluid, such as nitrous oxide, may be utilized. It may also be possible to use a liquid which has a relatively higher boiling point than the cryoablative fluid provided that all of the cryoablative fluid has previously boiled-off. Closing the actuatable valve within the exhaust block and measuring the pressure inside the liner is one way to detect if any of the cryoablative fluid remains where an increase in pressure would indicate the presence of liquid cryoablative fluid still boiling-off. Aside from forming an integrated fluid lumen into the liner, other mechanisms may instead be utilized to facilitate liner removal from the contacted tissue.

In these examples and any of the variations herein, a wire or heating element which may be warmed or energized (e.g., infrared) may be located on the probe shaft or positioned within the liner interior. Once the treatment procedure has been completed, the wire or heating element may be activated to warm the liner and the adjacent contacted tissue to facilitate the thawing of the tissue for removal of the liner.

Additionally and/or alternatively, the liner may be comprised of a lubricious liner or a separate non-stick coating may be applied to the liner exterior. It is not uncommon for polymers such as urethanes, especially thin films, to stick together if tightly-packed during sterilization, transportation and storage. The liner, being a thin polyurethane film compressed into a sheath, may employ a lubricious material or surface to ensure that the liner fully deploys and inflates following unsheathing.

Because optimal ablation coverage and depths may not be uniform over the entire contacted tissue region, the liner may be adjusted in thickness over particular regions of the liner to insulate predetermined tissue regions to result in tailored ablations. Ablation depths may be shallower where the liner is relatively thicker due to less efficient thermal transfer across the thicker areas.

In yet another variation, the liner may be designed with one or more predetermined weak points. If excessive tension were applied to the liner while it is frozen to tissue, the liner could tear. By locating one or more weakened regions of the liner near, e.g., the proximal connection to the probe shaft, the liner may be designed to tear specifically at the designated weakened regions which may make retrieval of the detached liner as a single piece relatively easier once the tissue fully thaws. In yet another variation of the liner, the liner may be separated into several individual liners in a multi-liner assembly.

In any of the variations described herein, the cooling probe may optionally include a compressible tip having a collapsible opening defined through the tip. The compressible tip may be positioned upon the distal tip of the probe located within the interior of the liner. Because the probe may be translatable within the liner and relative to the sheath, the tip may present a soft and atraumatic surface in the event the probe is advanced into contact against the interior of the liner and underlying tissue surface to prevent liner tears or trauma to the uterine tissue.

During a cryotherapy treatment, it is desirable to control the amount of the cryoablative fluid delivered into and through the liner. A few of the parameters which may affect the flow rate and volume of the cryoablative fluid discharged from the reservoir or canister may include temperature of the treatment assembly and reservoir or canister as well as ambient temperature in which the assembly is used as such temperatures can affect the internal pressure of the reservoir or canister. One method for controlling the starting cryogen pressure is by designing the system to operate at the high end of the temperature range and heating the reservoir or canister to a specified temperature and corresponding internal pressure. The heat could be supplied by a various mechanisms such as an electrical heating element wrapped around the reservoir or canister. In one variation, the electrical power for the heating element could be provided by a battery within the device itself.

In another variation, the electrical power may be provided by a heating cradle prior to device use. A separate warming cradle may define a receiving channel sized to receive the reservoir housing of the treatment assembly. The cradle may further include an electrical connector connected to an optional power supply (DC) (which may be recharged) and/or the cradle may be electrically connected to a stationary power supply via a power supply (AC) line. The cradle may also incorporate an optional stabilizing weight to provide for stability when the treatment assembly is docked within the receiving channel.

The treatment assembly itself may incorporate a heating element (e.g., a resistive heating element) which may be wrapped partially or entirely around the reservoir or canister. A layer of insulation may also be provided around the reservoir or canister to provide for a thermally stabilized warming environment. A temperature sensor (e.g., thermocouple, thermistor, etc.) may also be incorporated for thermal contact with the reservoir or canister for sensing the canister temperature. An electrical connector may be located correspondingly along the reservoir housing for electrically contacting the electrical connector positioned upon the cradle such that the cradle may provide electrical power to the treatment assembly when docked within the cradle receiving channel.

With the heating element and temperature sensor so coupled to the microprocessor or controller, the heating assembly may form a closed-loop system where the microprocessor or controller may be programmed via a software algorithm to control the electrical power supplied to the heating element depending upon the measured temperature of the temperature sensor such that the reservoir or canister is heated to a predetermined temperature or maintained within a predetermined temperature range prior to a cryotherapy treatment. The insulation may accordingly slow the rate of cooling of the reservoir or canister and also extend the available time between the removal of the treatment assembly from the cradle and the initiation of the treatment.

DETAILED DESCRIPTION OF THE INVENTION

Figure 1A:
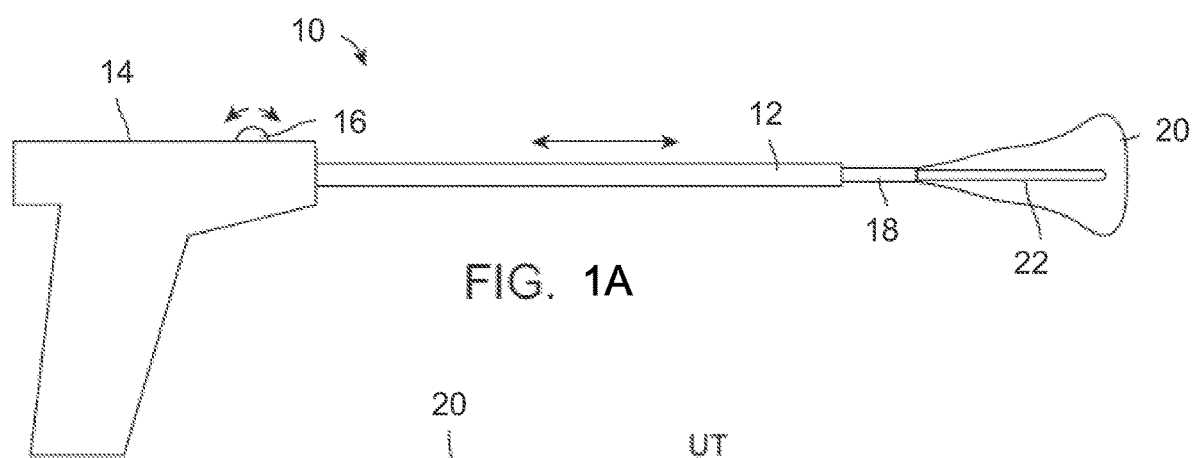
FIG. 1A shows a side view of an integrated treatment assembly.

The cooling probe 22 as well as the balloon assembly may be variously configured, for instance, in an integrated treatment assembly 10 as shown in the side view of FIG. 1A. In this variation, the assembly 10 may integrate the elongate shaft 18 having the liner or balloon 20 extending therefrom with the cooling probe 22 positioned translatably within the shaft 18 and liner 20. A separate translatable sheath 12 may be positioned over the elongate shaft 18 and both the elongate shaft 18 and sheath 12 may be attached to a handle assembly 14. The handle assembly 14 may further comprise an actuator 16 for controlling a translation of the sheath 12 for liner 20 delivery and deployment.

Figure 1B:
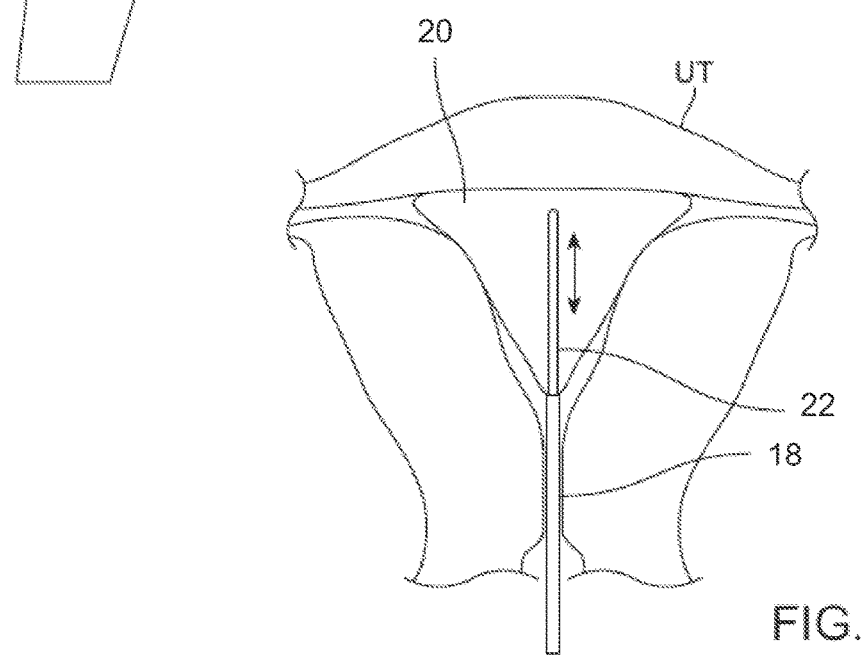
FIG. 1B shows an example of the assembly advanced through the cervix and into the uterus where the sheath may be retracted via the handle assembly to deploy the balloon.

With the sheath 12 positioned over the elongate shaft 18 and liner 20, the assembly 10 may be advanced through the cervix and into the uterus UT where the sheath 12 may be retracted via the handle assembly 14 to deploy the liner 20, as shown in FIG. 1B. As described above, once the liner 20 is initially deployed from the sheath 12, it may be expanded by an initial burst of a gas, e.g., air, carbon dioxide, etc., or by the cryoablative fluid. In particular, the tapered portions of the liner 20 may be expanded to ensure contact with the uterine cornu. The handle assembly 14 may also be used to actuate and control a longitudinal position of the cooling probe 22 relative to the elongate shaft 18 and liner 20 as indicated by the arrows.

Figure 1C:
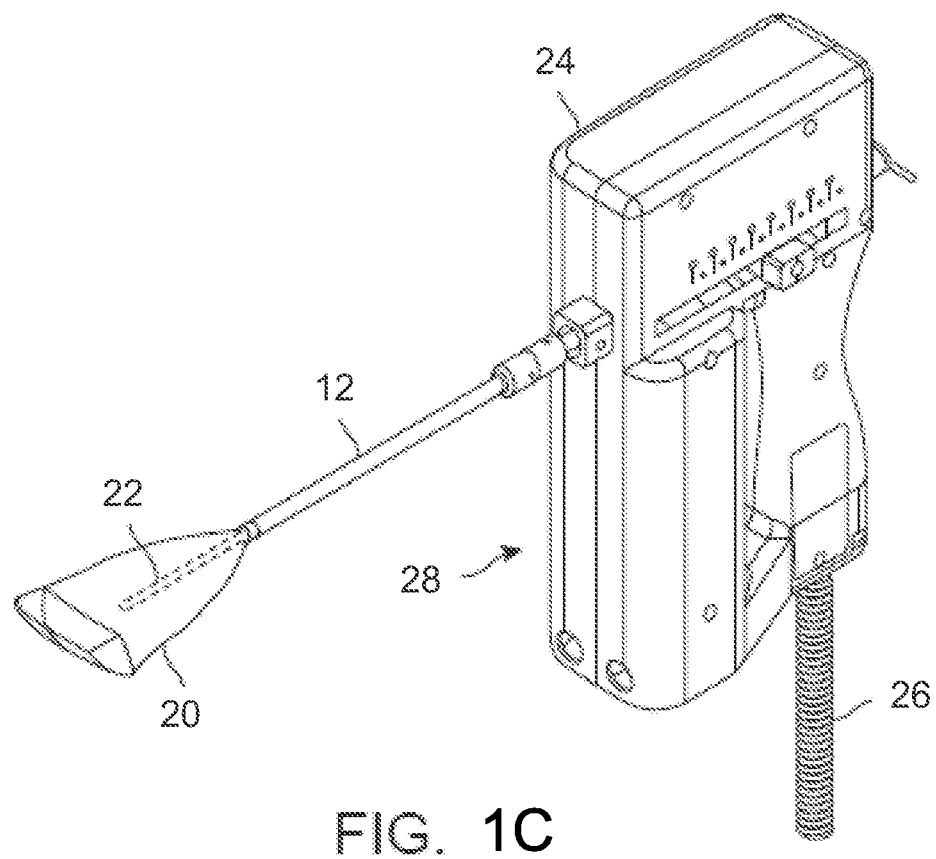
FIG. 1C shows a perspective view of a cryoablation assembly having a handle assembly which may integrate the electronics and pump assembly within the handle itself.

In another variation of the treatment assembly, FIG. 1C shows a perspective view of a cryoablation assembly having a handle assembly 24 which may integrate the electronics and pump assembly 28 within the handle itself. An exhaust tube 26 may also be seen attached to the handle assembly 24 for evacuating exhausted or excess cryoablative fluid or gas from the liner 20. Any of the cryoablative fluids or gases described herein may be utilized, e.g., compressed liquid-to-gas phase change of a compressed gas such as nitrous oxide ($N_2O$), carbon dioxide ($CO_2$), Argon, etc. The cooling probe 22 may be seen extending from sheath 12 while surrounded or enclosed by the liner or balloon 20. Hence, the handle assembly 24 with coupled cooling probe 22 and liner 20 may provide for a single device which may provide for pre-treatment puff-up or inflation of the liner 20, active cryoablation treatment, and/or post-treatment thaw cycles.

The handle assembly 24 may also optionally incorporate a display for providing any number of indicators and/or alerts to the user. For instance, an LCD display may be provided on the handle assembly 24 (or to a separate control unit connected to the handle assembly 24) where the display counts down the treatment time in seconds as the ablation is occurring. The display may also be used to provide measured pressure or temperature readings as well as any number of other indicators, symbols, or text, etc., for alerts, instructions, or other indications. Moreover, the display may be configured to have multiple color-coded outputs, e.g., green, yellow, and red. When the assembly is working through the ideal use case, the LED may be displayed as a solid green color. When the device requires user input (e.g. when paused and needing the user to press the button to re-start treatment) the LED may flash or display yellow. Additionally, when the device has faulted and treatment is stopped, the LED may flash or display a solid red color.

Figure 1D:
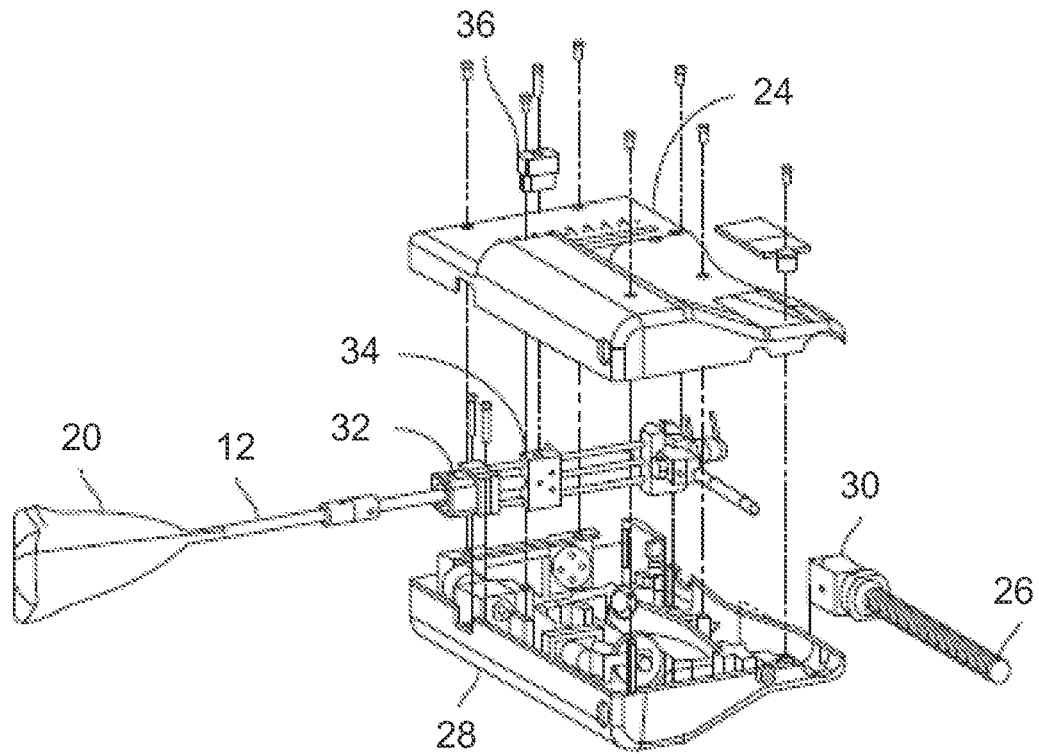
FIG. 1D shows the handle assembly in a perspective exploded view illustrating some of the components which may be integrated within the handle.

FIG. 1D shows the handle assembly 24 in a perspective exploded view to illustrate some of the components which may be integrated within the handle 24. As shown, the liner 20 and sheath 12 may be coupled to a sheath bearing assembly 32 and slider base block assembly 34 for controlling the amount of exposed treatment length along the cooling probe 22 (and as described in further detail below). An actuatable sheath control 36 may be attached to the slider base block assembly 34 for manually controlling the treatment length of the cooling probe 22 as well. Along with the electronics and pump assembly 28 (which may optionally incorporate a programmable processor or controller in electrical communication with any of the mechanisms within the handle 24), an exhaust valve 30 (e.g., actuated via a solenoid) may be coupled to the exhaust line 26 for controlling not only the outflow of the exhausted cryoablation fluid or gas but also for creating or increasing a backpressure during treatment, as described in further detail below.

Figure 1E:
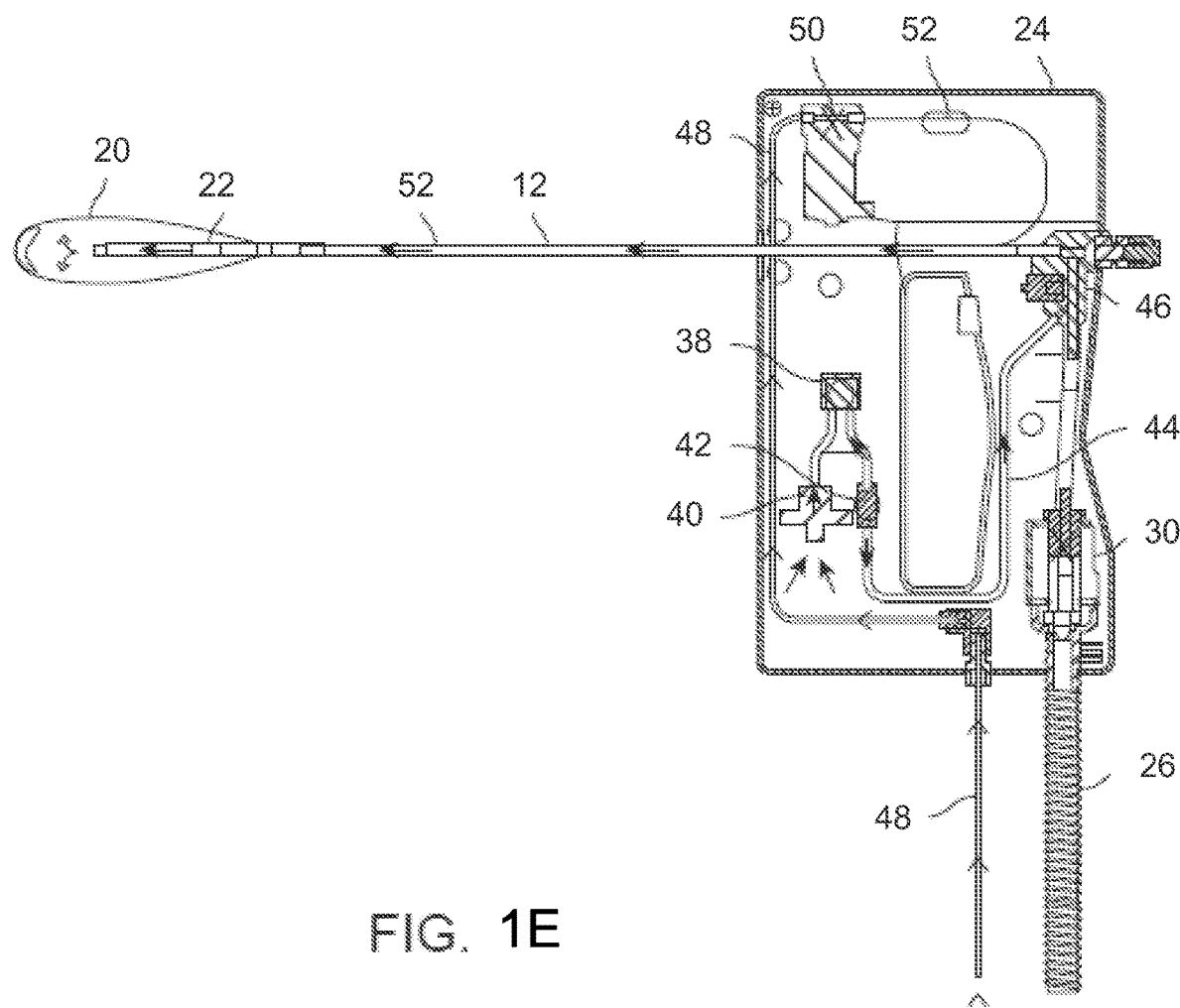
FIG. 1E shows an example of the system operation during a pre-treatment puff up process.
Figure 1F:
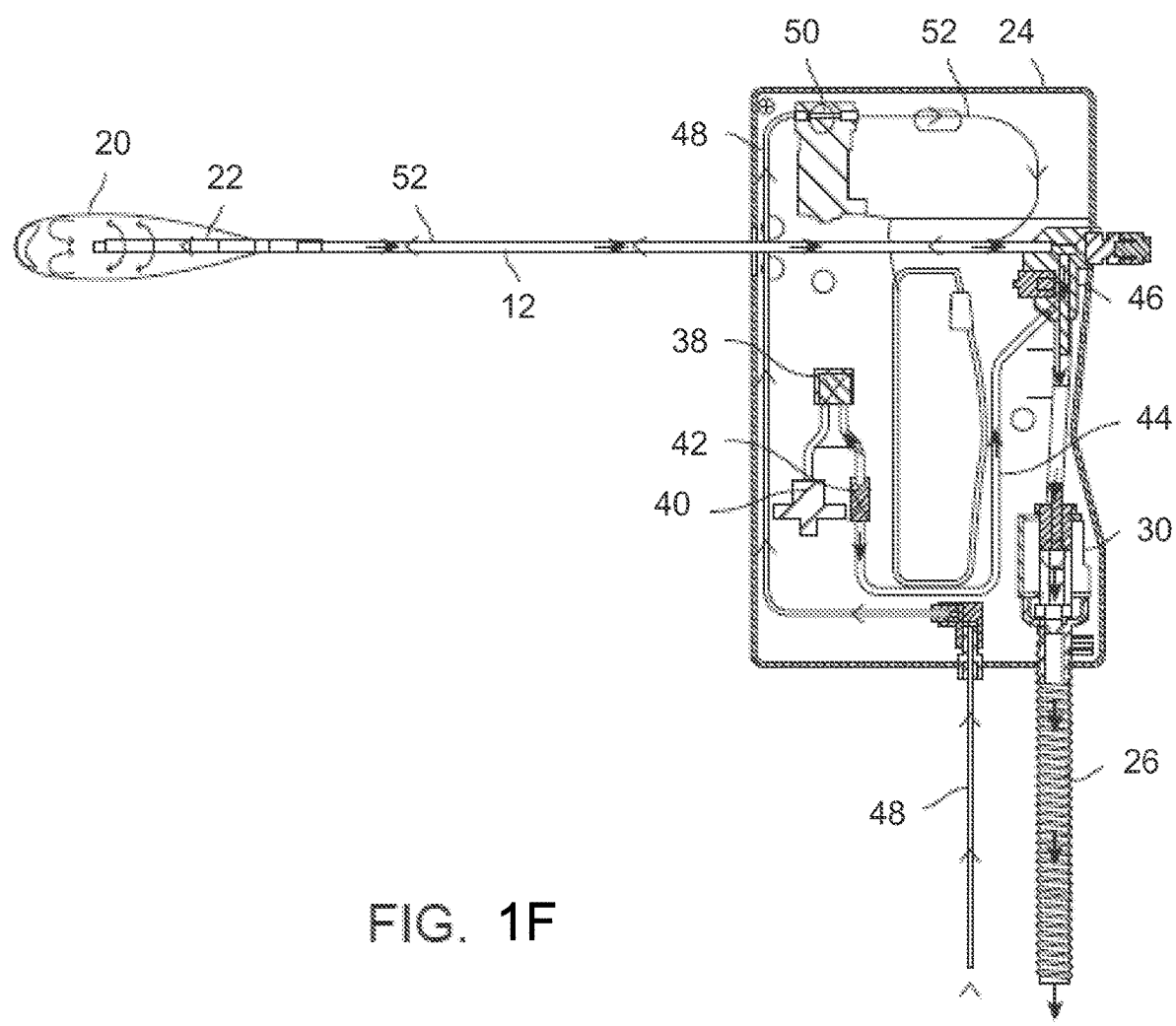
FIG. 1F shows an example of the system operation during a treatment process.
Figure 1G:
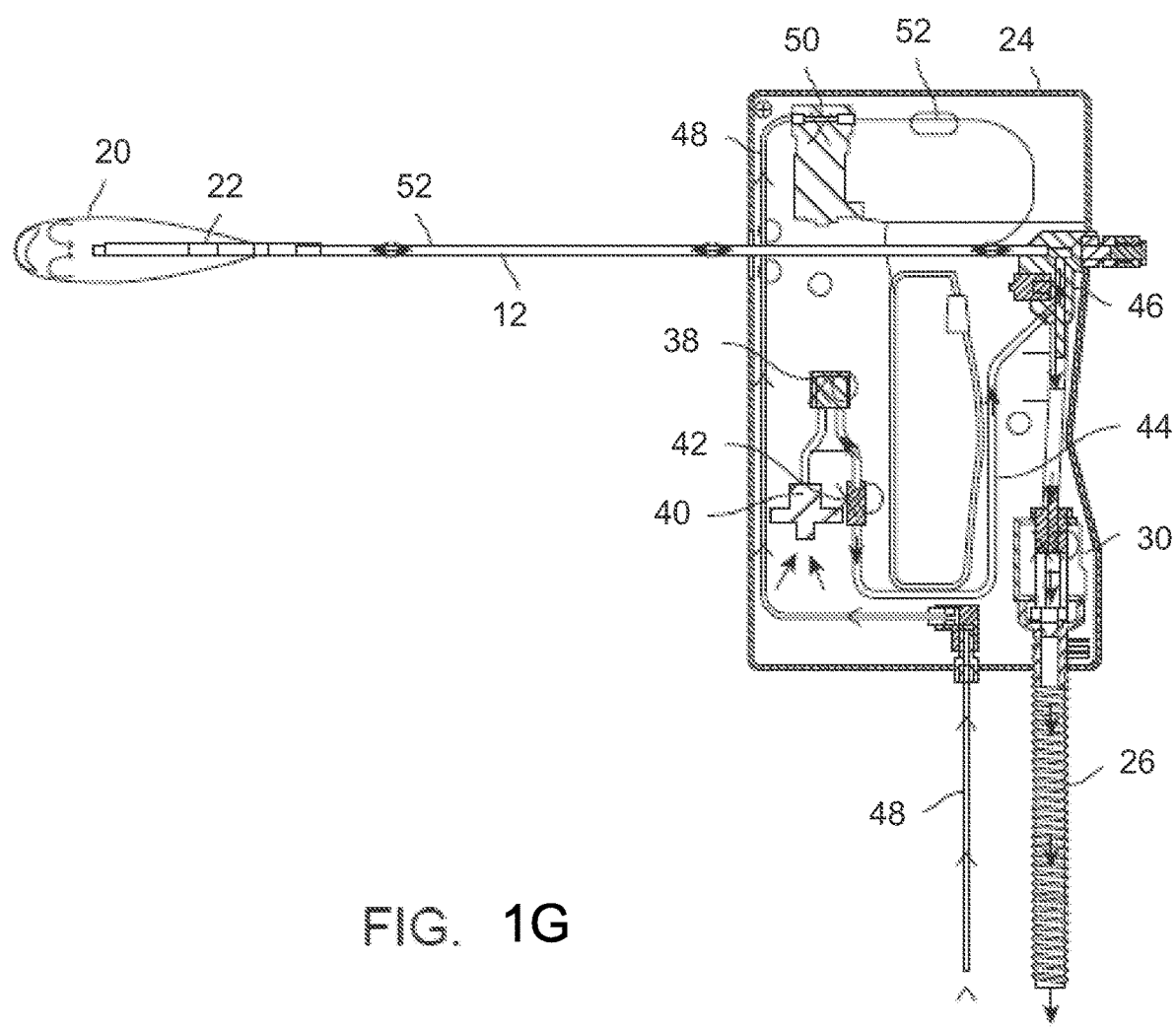
FIG. 1G shows an example of the system operation during a thawing and venting process.

In one example of how the handle assembly 24 may provide for treatment, FIGS. 1E to 1G illustrate schematic side views of how the components may be integrated and utilized with one another. As described herein, once the sheath 12 and/or liner 20 has been advanced and initially introduced into the uterus, the liner 20 may be expanded or inflated in a pre-treatment puff up to expand the liner 20 into contact against the uterine tissue surfaces in preparation for a cryoablation treatment. As illustrated in the side view of FIG. 1E, a pump 38 integrated within the handle assembly 24 may be actuated and a valve 42 (e.g., actuatable or passive) fluidly coupled to the pump 38 may be opened (as indicated schematically by an "O" over both the pump 38 and valve 42) such that ambient air may be drawn in through, e.g., an air filter 40 integrated along the handle 24, and passed through an air line 44 within the handle and to an exhaust block 46. The exhaust block 46 and air line 44 may be fluidly coupled to the tubular exhaust channel which extends from the handle 24 which is further attached to the cooling probe 22. As the air is introduced into the interior of the liner 20 (indicated by the arrows), the liner 20 may be expanded into contact against the surrounding uterine tissue surface.

A cryoablative fluid line 48 also extending into and integrated within the handle assembly 24 may be fluidly coupled to an actuatable valve 50, e.g., actuated via a solenoid, which may be manually closed or automatically closed (as indicated schematically by an "X" over the valve 50) by a controller to prevent the introduction of the cryoablative fluid or gas into the liner 20 during the pre-treatment liner expansion. An infusion line 52 may be fluidly coupled to the valve 50 and may also be coupled along the length of the sheath 12 and probe 22, as described in further detail below. The exhaust valve 30 coupled to the exhaust line 26 may also be closed (as indicated schematically by an "X" over the valve 30) manually or automatically by the controller to prevent the escape of the air from the exhaust block 46.

During this initial liner expansion, the liner 20 may be expanded in a gradual and controlled manner to minimize any pain which may be experienced by the patient in opening the uterine cavity. Hence, the liner 20 may be expanded gradually by metering in small amounts of air. Optionally, the pump 38 may be programmed and controlled by a processor or microcontroller to expand the liner 20 according to an algorithm (e.g., e.g. ramp-up pressure quickly to 10 mm Hg and then slow-down the ramp-up as the pressure increases to 85 mm Hg) which may be stopped or paused by the user. Moreover, the liner 20 may be expanded to a volume which is just sufficient to take up space within the uterine cavity. After the initial increase in pressure, the pressure within the liner 20 may be optionally increased in bursts or pulses. Moreover, visualization (e.g., via a hysteroscope or abdominal ultrasound) may be optionally used during the controlled gradual expansion to determine when the uterine cavity is fully open and requires no further pressurization. In yet another variation, the liner 20 may be cyclically inflated and deflated to fully expand the liner. The inflations and deflations may be partial or full depending upon the desired expansion.

In yet another alternative variation, the system could also use an amount of air pumped into the liner 20 as a mechanism for detecting whether the device is in a false passage of the body rather than the uterine cavity to be treated. The system could use the amount of time that the pump 38 is on to track how much air has been pushed into the liner 20. If the pump 38 fails to reach certain pressure levels within a predetermined period of time, then the controller may indicate that the device is positioned within a false passage. There could also be a limit to the amount of air allowed to be pushed into the liner 20 as a way to detect whether the probe 22 has been pushed, e.g., out into the peritoneal cavity. If too much air is pushed into the liner 20 (e.g., the volume of air tracked by the controller exceeds a predetermined level) before reaching certain pressures, then the controller may indicate the presence of a leak or that the liner 20 is not fully constrained by the uterine cavity. The liner 20 may also incorporate a release feature which is configured to rupture if the liner 20 is not constrained such that if the system attempts to pump up the liner 20 to treatment pressure (e.g., 140 mmHg), the release feature will rupture before reaching that pressure.

Once the liner 20 has been expanded sufficiently into contact against the uterine tissue surface, the cryoablation treatment may be initiated. As shown in the side view of FIG. 1F, the air pump 38 may be turned off and the valve 42 may be closed (as indicated schematically by an "X" over the pump 38 and valve 42) to prevent any further infusion of air into the liner 20. With the cryoablative fluid or gas pressurized within the line 48, valve 50 may be opened (as indicated schematically by an "O" over the valve 50) to allow for the flow of the cryoablative fluid or gas to flow through the infusion line 52 coupled to the valve 50. Infusion line 52 may be routed through or along the sheath 12 and along the probe 22 where it may introduce the cryoablative fluid or gas within the interior of liner 20 for infusion against the liner 20 contacted against the surrounding tissue surface.

During treatment or afterwards, the exhaust valve 30 may also be opened (as indicated schematically by an "O" over the valve 30) to allow for the discharged fluid or gas to exit or be drawn from the liner interior and proximally through the cooling probe 22, such as through the distal tip opening. The fluid or gas may exit from the liner 20 due to a pressure differential between the liner interior and the exhaust exit and/or the fluid or gas may be actively drawn out from the liner interior, as described in further detail herein. The spent fluid or gas may then be withdrawn proximally through the probe 22 and through the lumen surrounded by the sheath 12, exhaust block 46, and the exhaust tube 26 where the spent fluid or gas may be vented. With the treatment fluid or gas thus introduced through infusion line 52 within the liner 20 and then withdrawn, the cryoablative treatment may be applied uninterrupted.

Once a treatment has been completed, the tissue of the uterine cavity may be permitted to thaw. During this process, the cryoablative fluid delivery is halted through the infusion line 52 by closing the valve 50 (as indicated schematically by an "X" over the valve 50) while continuing to exhaust for any remaining cryoablative fluid or gas remaining within the liner 20 through probe 22, through the lumen surrounded by sheath 12, and exhaust line 26, as shown in FIG. 1G. Optionally, the pump 38 and valve 42 may be cycled on and off and the exhaust valve 30 may also be cycled on and off to push ambient air into the liner 20 to facilitate the thawing of the liner 20 to the uterine cavity. Optionally, warmed or room temperature air or fluid (e.g., saline) may also be pumped into the liner 20 to further facilitate thawing of the tissue region.

As the spent cryoablative fluid or gas is removed from the liner 20, a drip prevention system may be optionally incorporated into the handle. For instance, a passive system incorporating a vented trap may be integrated into the handle which allows exhaust gas to escape but captures any vented liquid. The exhaust line 26 may be elongated to allow for any vented liquid to evaporate or the exhaust line 26 may be convoluted to increase the surface area of the exhaust gas tube to promote evaporation.

Alternatively, an active system may be integrated into the handle or coupled to the handle 24 where a heat sink may be connected to a temperature sensor and electrical circuit which is controlled by a processor or microcontroller. The heat sink may promote heat transfer and causes any liquid exhaust to evaporate. When the temperature of the heat sink reaches the boiling temperature of, e.g., nitrous oxide (around −86° C.), the handle may be configured to slow or stop the delivery of the cryoablative fluid or gas to the uterine cavity.

The pre-treatment infusion of air as well as the methods for treatment and thawing may be utilized with any of the liner, probe, or apparatus variations described herein. Moreover, the pre-treatment, treatment, or post-treatment procedures may be utilized altogether in a single procedure or different aspects of such procedures may be used in varying combinations depending upon the desired results.

Additionally and/or optionally, the handle 24 may incorporate an orientation sensor to facilitate maintaining the handle 24 in a desirable orientation for treatment. One variation may incorporate a ball having a specific weight covering the exhaust line 26 such that when the handle 24 is held in the desirable upright orientation, the treatment may proceed uninterrupted. However, if the handle 24 moved out of its desired orientation, the ball may be configured to roll out of position and trigger a visual and/or auditory alarm to alert the user. In another variation, an electronic gyroscopic sensor may be used to maintain the handle 24 in the desired orientation for treatment.

Figure 2A:
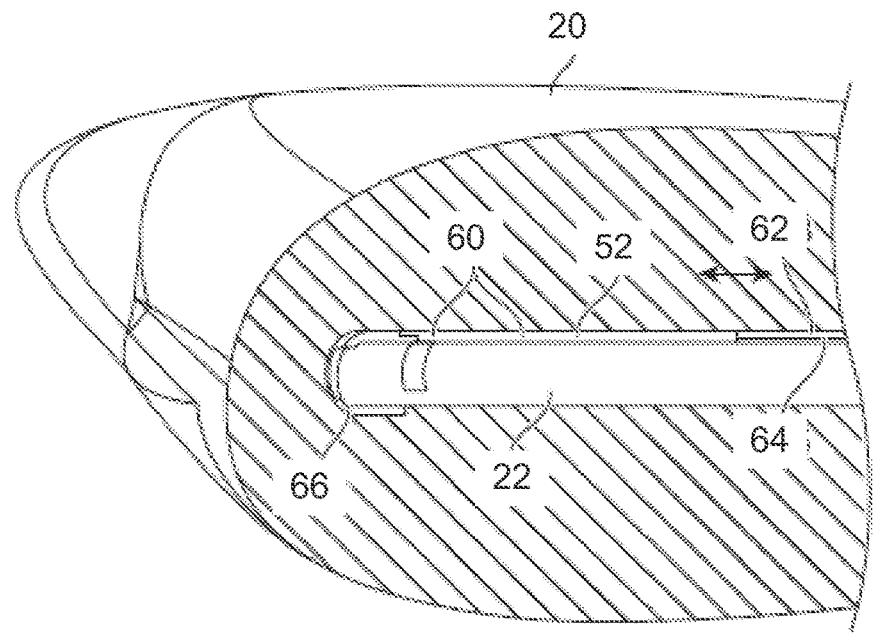
FIGS. 2A and 2B show cross-sectional side views of yet another variation of a cooling probe which utilizes a single infusion line in combination with a translatable delivery line.
Figure 2B:
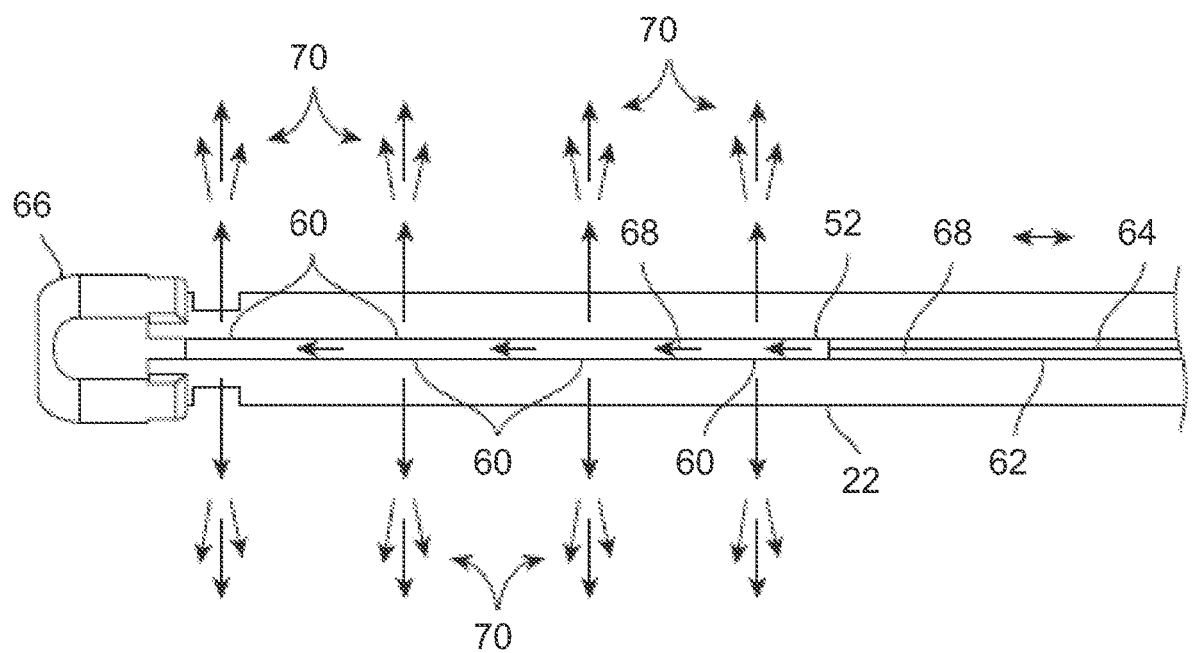

FIGS. 2A and 2B show cross-sectional side views of yet another variation of a cooling probe which utilizes a single infusion line in combination with a translatable delivery line. To accommodate various sizes and shapes of uterine cavities, the cooling probe may have a sliding adjustment that may be set, e.g., according to the measured length of the patient's uterine cavity. The adjustment may move along the sheath along the exhaust tube as well as the delivery line within the infusion line. The sheath may constrain the liner 20 and also control its deployment within the cavity.

In this variation, an infusion line 52 (as described above) may pass from the handle assembly and along or within the sheath and into the interior of liner 20. The infusion line 52 may be aligned along the probe 22 such that the infusion line 52 is parallel with a longitudinal axis of the probe 22 and extends towards the distal tip 66 of the probe 22. Moreover, the infusion line 52 may be positioned along the probe 22 such that the line 52 remains exposed to the corners of the liner 20 which extend towards the cornua. With the infusion line 52 positioned accordingly, the length of the line 52 within the liner 20 may have multiple openings formed along its length which act as delivery ports for the infused cryoablative fluid or gas. A separate translating delivery line 64, e.g., formed of a Nitinol tube defining an infusion lumen therethrough, may be slidably positioned through the length of the infusion line 52 such that the delivery line 64 may be moved (as indicated by the arrows in FIG. 2A) relative to the infusion line 52 which remains stationary relative to the probe 22.

The openings along the length of the infusion line 52 may be positioned such that the openings are exposed to the sides of the interior of the liner 20, e.g., cross-drilled. As the cryoablative fluid or gas is introduced through the delivery line 64, the infused cryoablative fluid or gas 68 may pass through the infusion line 52 and then out through the openings defined along the infusion line 52. By adjusting the translational position of the delivery line 64, the delivery line 64 may also cover a selected number of the openings resulting in a number of open delivery ports 60 as well as closed delivery ports 62 which are obstructed by the delivery line 64 position relative to the infusion line 52, as shown in the top view of FIG. 2B.

By translating the delivery line 64 accordingly, the number of open delivery ports 60 and closed delivery ports 62 may be adjusted depending on the desired treatment length and further ensures that only desired regions of the uterine tissue are exposed to the infused cryoablative fluid or gas 68. Once the number of open delivery ports 60 has been suitably selected, the infused cryoablative fluid or gas 68 may bypass the closed delivery ports 62 obstructed by the delivery line 64 and the fluid or gas may then be forced out through the open delivery ports 60 in a transverse direction as indicated by the infusion spray direction 70. The terminal end of the infusion line 52 may be obstructed to prevent the distal release of the infused fluid or gas 68 from its distal end. Although in other variations, the terminal end of the infusion line 52 may be left unobstructed and opened.

Figure 3A:
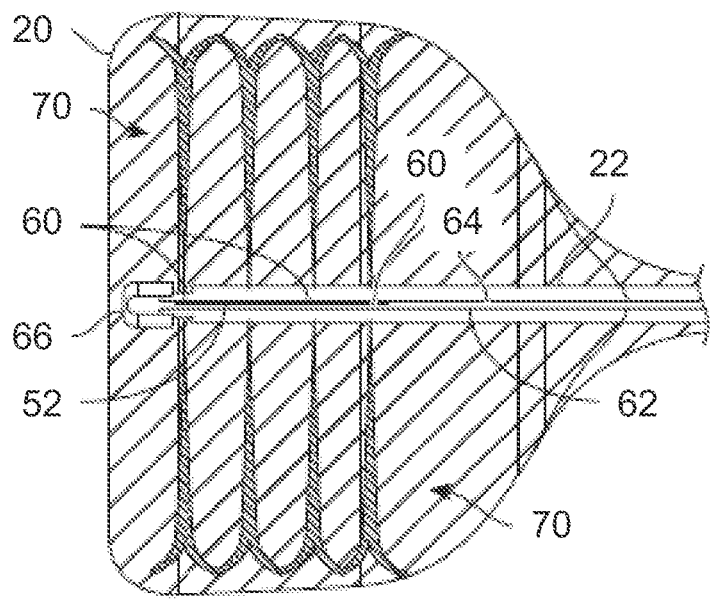
FIGS. 3A and 3B show top and perspective views of the expanded liner with four pairs of the open delivery ports exposed in apposed direction.
Figure 3B:
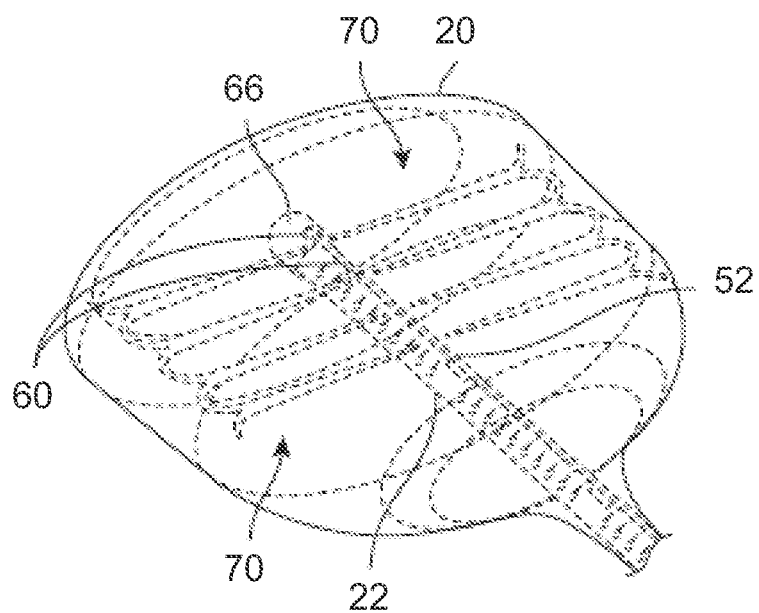

FIGS. 3A and 3B show top and perspective views of the expanded liner 20 with four pairs of the open delivery ports 60 exposed in apposed direction. Because the infused fluid or gas 68 may be injected into the liner 20, e.g., as a liquid, under relatively high pressure, the injected cryoablative liquid may be sprayed through the open delivery ports 60 in a transverse or perpendicular direction relative to the cooling probe 22. The laterally infused cryoablative fluid 70 may spray against the interior of the liner 20 (which is contacted against the surrounding tissue surface) such that the cryoablative liquid 70 coats the interior walls of the liner 20 due to turbulent flow causing heavy mixing. As the cryoablative liquid 70 coats the liner surface, the sprayed liquid 70 may absorb heat from the tissue walls causing rapid cooling of the tissue while also evaporating the liquid cryogen to a gas form that flows out through the cooling probe 22. This rapid cooling and evaporation of the cryoablative liquid 70 facilitates the creation of a fast and deep ablation over the tissue. During treatment, the temperature within the cavity typically drops, e.g., −86° C., within 2-3 seconds after the procedure has started. While the interior walls of the liner 20 are first coated with the cryoablative liquid 70, a portion of the cryoablative liquid 70 may no longer change phase as the procedure progresses.

While four pairs of the open delivery ports 60 are shown, the number of exposed openings may be adjusted to fewer than four pairs or more than four pairs depending on the positioning of the delivery line 64 and also the number of openings defined along the infusion line 52 as well as the spacing between the openings. Moreover, the positioning of the openings may also be adjusted such that the sprayed liquid 70 may spray in alternative directions rather than laterally as shown. Additionally and/or alternatively, additional openings may be defined along other regions of the infusion line 52.

Further variations of the treatment assembly features and methods which may be utilized in combination with any of the features and methods described herein may be found in the following patent applications:

U.S. patent application Ser. No. 13/361,779 filed Jan. 30, 2012 (US Pub. 2012/0197245);

U.S. patent application Ser. No. 13/900,916 filed May 23, 2013 (US Pub. 2013-0296837);

U.S. patent application Ser. No. 14/019,898 filed Sep. 6, 2013 (US Pub. 2014/0012156);

U.S. patent application Ser. No. 14/019,928 filed Sep. 6, 2013 (US Pub. 2014/005648);

U.S. patent application Ser. No. 14/020,265 filed Sep. 6, 2013 (US Pub. 2014/0005649);

U.S. patent application Ser. No. 14/020,306 filed Sep. 6, 2013 (US Pub. 2014/0025055);

U.S. patent application Ser. No. 14/020,350 filed Sep. 6, 2013 (US Pub. 2014/0012244);

U.S. patent application Ser. No. 14/020,397 filed Sep. 6, 2013 (US Pub. 2014/0012243);

U.S. patent application Ser. No. 14/020,452 filed Sep. 6, 2013 (US Pub. 2014/0005650);

U.S. patent application Ser. No. 14/086,050 filed Nov. 21, 2013 (US Pub. 2014/0074081);

U.S. patent application Ser. No. 14/086,088 filed Nov. 21, 2013 (US Pub. 2014/0088579); and U.S. patent application Ser. No. 14/029,641 filed Sep. 17, 2013.

Each of the patent applications above is incorporated herein by reference in its entirety and for any purpose herein.

Figure 4A:
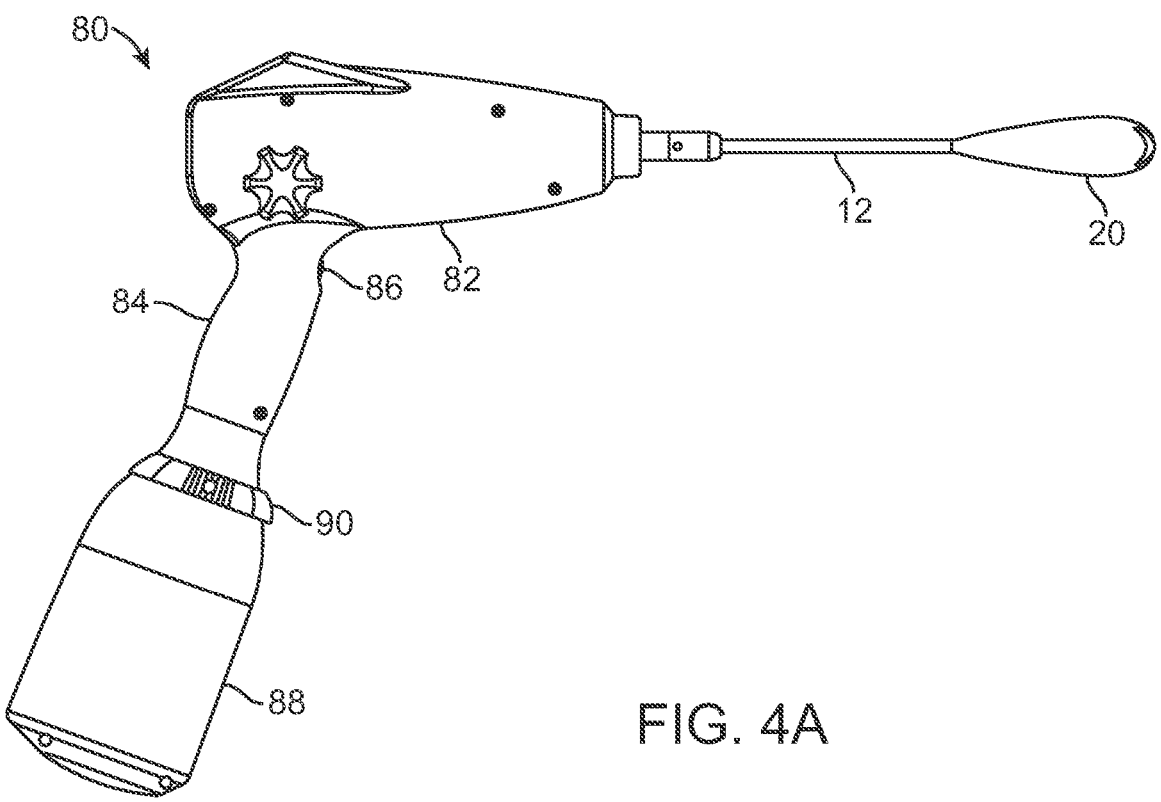
FIGS. 4A to 4C show side and assembly views of another variation of the treatment assembly.
Figure 4B:
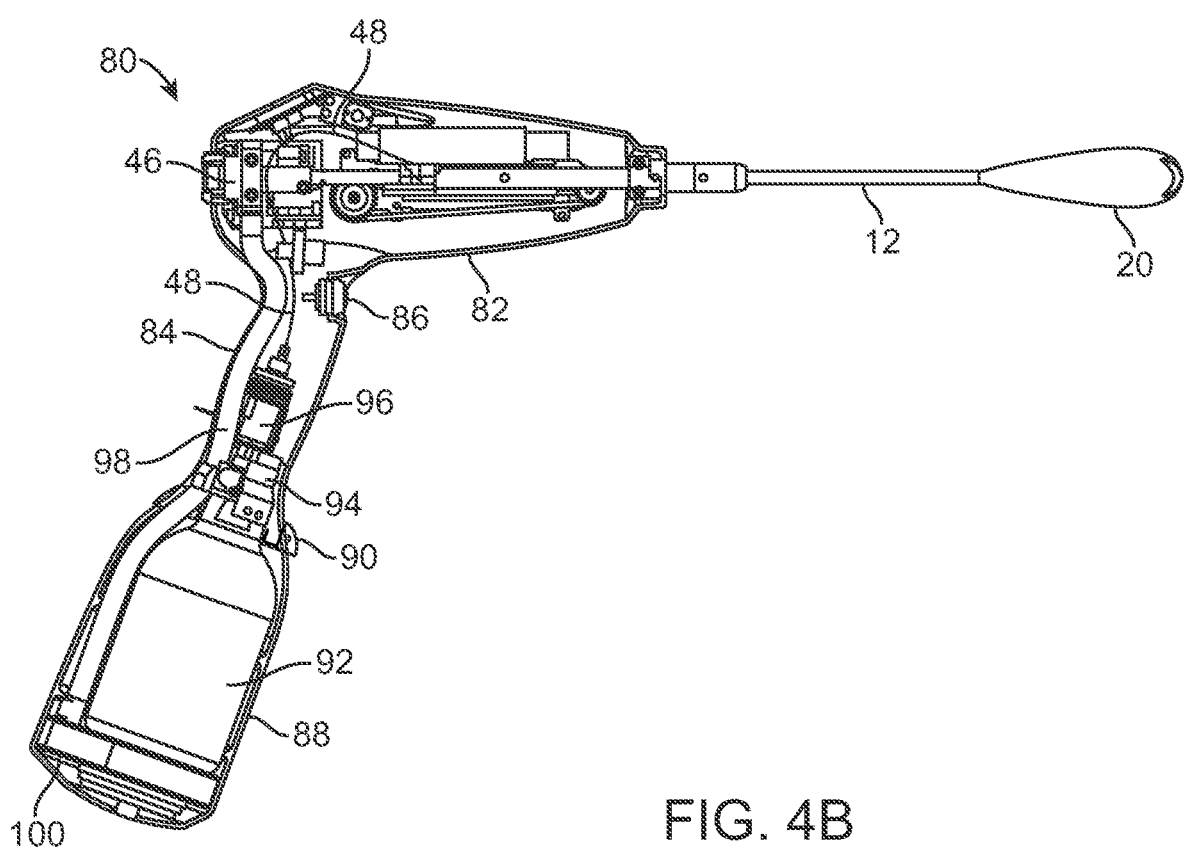
Figure 4C:
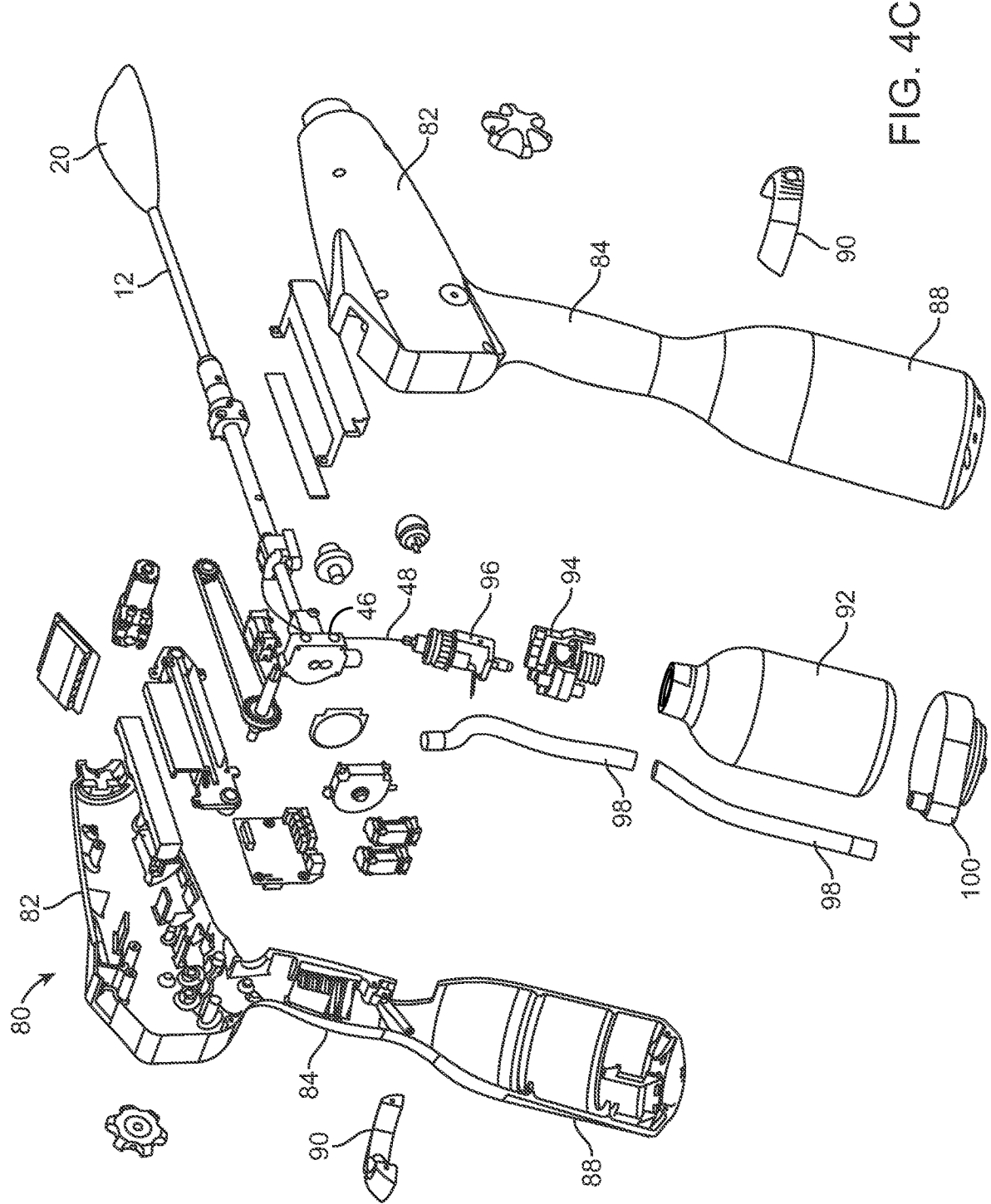

Yet another variation of the treatment assembly 80 is shown in the side and partial cross-sectional side views of FIGS. 4A and 4B which illustrate a housing 82 having a handle 84 and a reservoir housing 88 extending from and attached directly to the handle 84. FIG. 4C further illustrates a perspective assembly view of the treatment assembly 80 and some of its components contained internally.

The sheath 12 having the liner 20 may extend from the housing 82 while an actuator 86 may be located, for instance, along the handle 84 to enable the operator to initiate the cryoablative treatment. A reservoir or canister 92 fully containing the cryoablative agent (as described herein) may be inserted and retained within the reservoir housing 88. The reservoir housing 88 and/or the handle 84 may further incorporate a reservoir engagement control 90 which may be actuated, e.g., by rotating the control 90 relative to the handle 84, to initially open fluid communication with the reservoir or canister 92 to charge the system for treatment.

The reservoir or canister 92 may be inserted into the reservoir housing 88 and into secure engagement with a reservoir or canister valve 94 which may be coupled to the reservoir engagement control 90. The valve 94 may be adjusted to open the reservoir or canister 92 for treatment or for venting of the discharged cryoablative agent during or after treatment. An inflow modulation control unit 96 (e.g., an actuatable solenoid mechanism) may be coupled directly to the reservoir or canister valve 94 and the cryoablative fluid line 48 may be coupled directly to the modulation control unit 96 and through the sheath 12 and into fluid communication within the liner 20, as described herein.

During or after treatment, the discharged cryoablative fluid may be evacuated through the exhaust block 46 contained within the housing and then through the exhaust line 98 coupled to the exhaust block 46. The exhaust line 98 may extend through the handle 84 and the reservoir housing 88 and terminate at an exhaust line opening 100 which may be attached to another exhaust collection line, as further described herein.

Inflow Modulation Control

Figure 5:
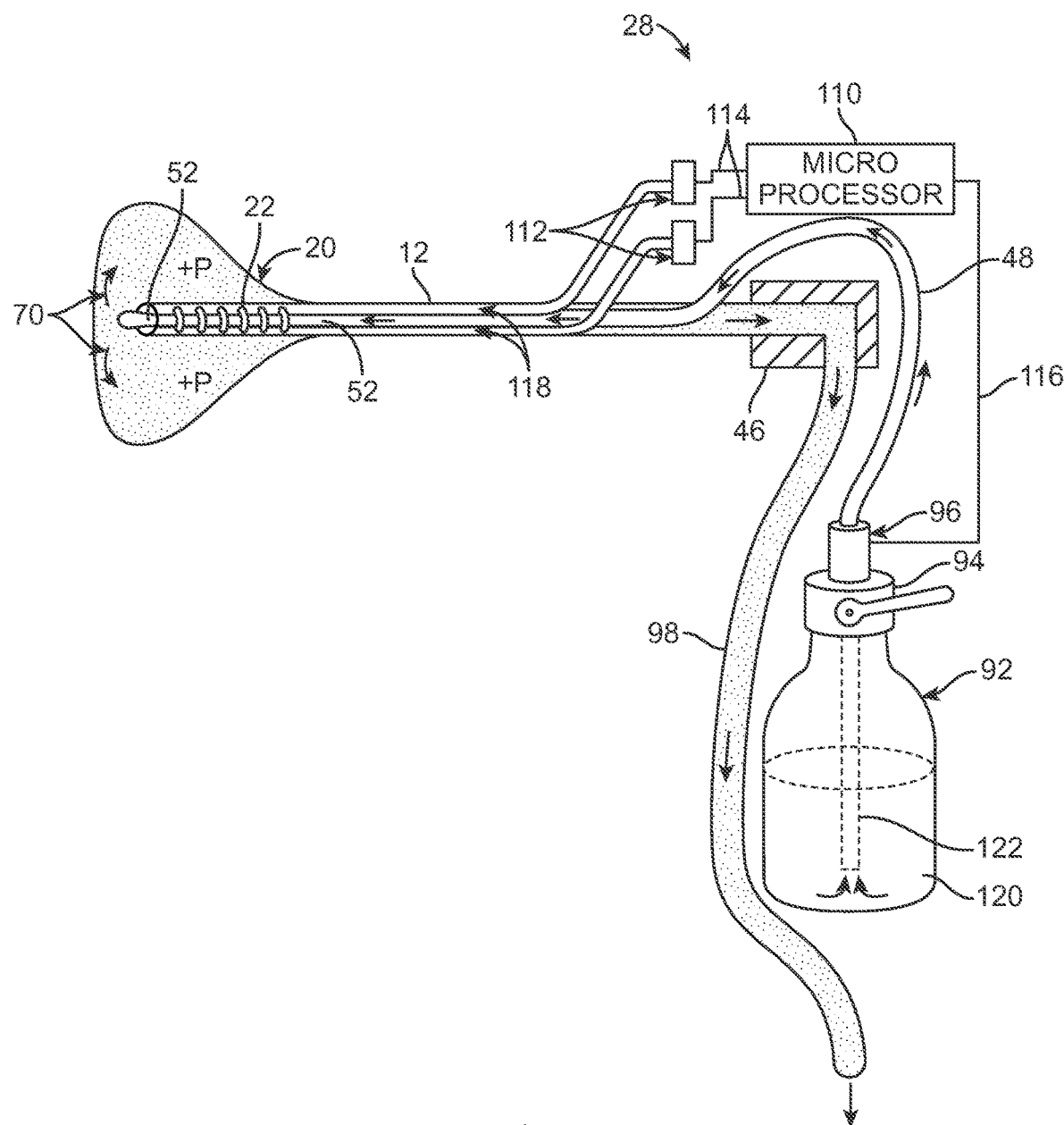
FIG. 5 shows a schematic illustration of a treatment assembly having a modulated inflow valve.

The reservoir or canister valve 94 and modulation control unit 96 are further illustrated in the schematic view of FIG. 5 which shows the modulation control unit 96 in electrical communication with microprocessor or controller 110 (which may be part of the electronics and pump assembly 28) via electrical line 116. As shown, the inflow of the cryoablative agent 120 contained within the reservoir or canister 92 may flow through an inflow line 122 within the canister 92 and through the reservoir or canister valve 94 and modulation control unit 96 and into cryoablative fluid line 48 for introduction within the liner 20 via infusion line 52, as described herein.

One or more pressure measurement lines 118 which are in fluid communication with the interior of the liner 20 may extend through the sheath 12 and in communication with corresponding pressure sensors 112 which in turn are in electrical communication with microprocessor or controller 110 via electrical lines 114. The pressure sensed by the measurement lines 118 may be due (at least in part) to the expansion of the cryoablative agent 120 (e.g., nitrous oxide) which contacts the interior walls of the liner 20, as described herein. Hence, microprocessor or controller 110 may actively control the modulation control unit 96 in a corresponding manner based on the detected pressure values within the liner 20 sensed via pressure sensors 112.

It is desirable to control the pressure within the liner 20 when positioned within the uterine cavity to minimize patient discomfort while simultaneously ensuring that the liner 20 remains fully deployed and in contact with the endometrial tissue. A pressure of about, e.g., 140 mmHg, is near the maximum pressure typically used during a hysteroscopy and is well-tolerated by most patients. However, other endometrial ablation devices may have operating pressures of up to 180 mmHg to 220 mmHg (or more) but such therapies typically require that the patients receive sedation due to hyperthermic ablation and high uterine pressures.

Hence, to maximize patient comfort, the liner 20 may be initially inflated with air to about, e.g., 140 mmHg, prior to the infusion of the cryoablative agent 120, as also described herein. However, once the cryoablative agent 120 is introduced into the liner 20, the transition from air to the cryoablative agent 120 may create a brief fluctuation in the intracavitary pressure, e.g., spike or dip in the pressure. For instance, the pressure with which the cryoablative agent 120 is introduced may initially be relatively higher, e.g., about 130 mmHg. Over the course of the treatment procedure, e.g., 150 second, the pressure within the liner 20 may result in a relatively lower pressure, e.g., about 95 mmHg.

Various factors may have an influence on the pressure fluctuation over the course of the treatment procedure. For example, the initial pressure within the reservoir or canister 92 (e.g., nitrous oxide cylinder or tank) may have an impact on the pressure within the liner 20 during treatment. Conditions such as ambient temperature and/or temperature of the reservoir or canister may also have an influence. For instance, the warmer the device temperature, the greater the cylinder pressure and cryoablative agent 120 flow rate and, correspondingly, the greater the intrauterine pressure.

Hence, the internal pressure within the liner 20 during treatment may be controlled by the microprocessor or controller 110 which may modulate the reservoir or canister valve 94 via the modulation control unit 96 (e.g., a solenoid valve or other mechanism) in response to the intracavitary pressures sensed by the pressure sensors 112. This closed-loop system may incorporate, for instance, dual pressure measuring tubes 118 and corresponding sensors 112 as both a redundant safety system and to also identify possible erroneous data points. The closed-loop control system can be controlled by a PID or non-PID software algorithm via the microprocessor or controller 110. Additionally, the modulation control unit 96 may be used controlled by the microprocessor or controller 110 to control the flow rate of the cryoablative agent 120 during the treatment procedure to optimize ablation depth and minimize the amount of cryoablative agent needed.

Evacuation Control

Figure 6:
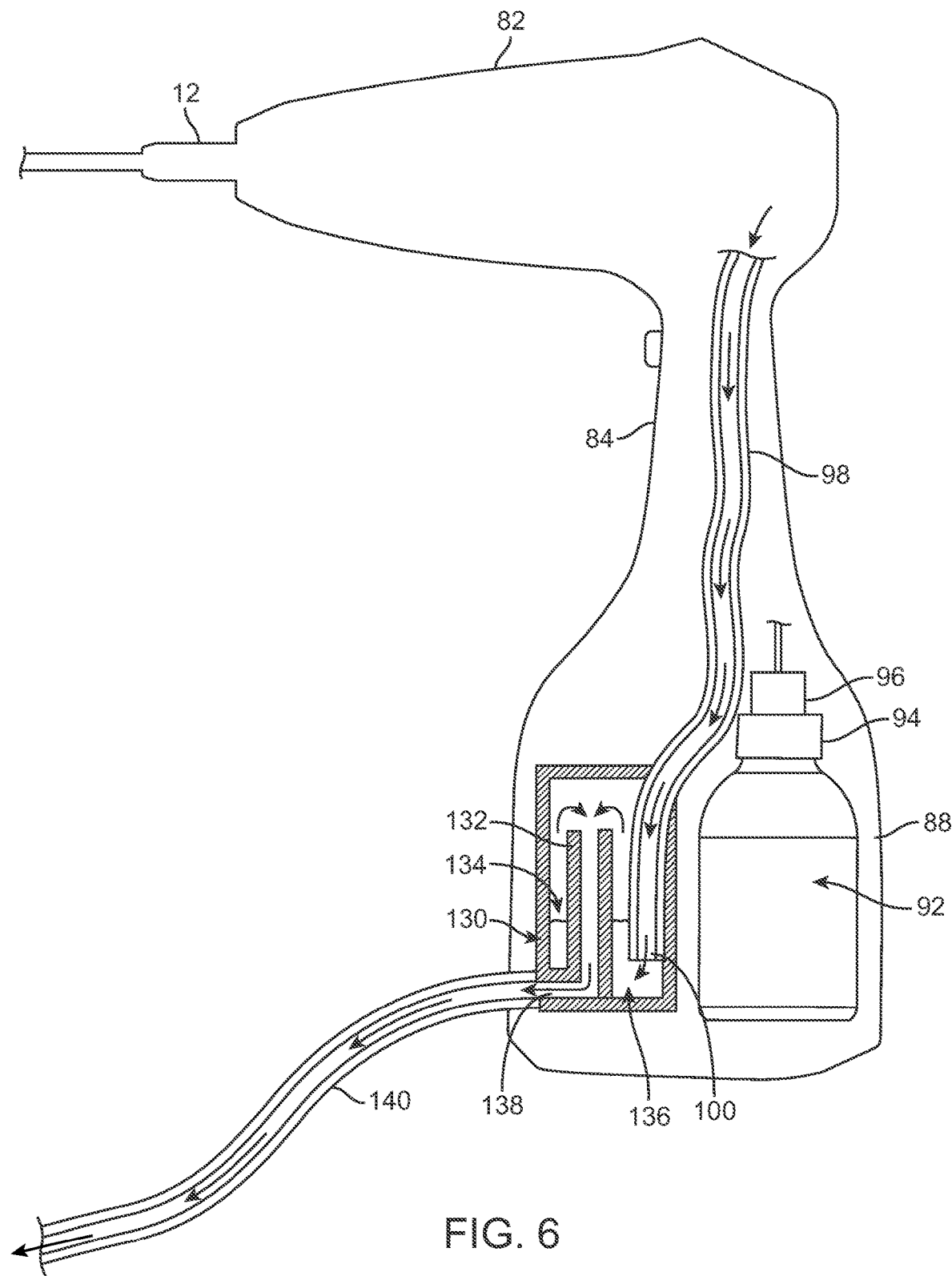
FIG. 6 shows a schematic illustration of a treatment assembly having a ventilation trap which also acts as a heat sink.

During or after the treatment procedure, the discharged cryoablative agent 120 evacuated from the interior of the liner 20 passes through the exhaust line 98 which may run through the handle 84 and reservoir housing 88, as further shown in the schematic illustration in FIG. 6. At some point during a cryoablation procedure, it may not be uncommon for the cryoablative agent still in a liquid phase to appear in the exhaust gas passing through exhaust line 98. Having the exhaust remain in droplets of liquid nitrous oxide could potentially pose a hazard to patients by coming into contact with the patient's or user's skin and larger drops of the liquid cryoablative agent could potentially cause burns. Hence, a system for ensuring that the discharged cryoablative agent passing through the exhaust line 98 is fully evaporated can be incorporated into the treatment assembly.

In the variation shown, a liquid exhaust trap 130 which may also function as a heatsink for converting any present liquid cryogen into a gas may be integrated, for instance, directly into the reservoir housing 88 or handle 84. Such a liquid exhaust trap 130 may generally include a fluid trap 134 near the bottom portion of the liquid exhaust trap 130 where the exhaust line opening 100 may be positioned. An exhaust lumen 132 may extend within the liquid exhaust trap 130 from the fluid trap 134 and the exhaust lumen 132 may further define an opening which is clear of any fluid which may collected within the fluid trap 134. An evacuating exhaust line 140 may be coupled to an opening 138 in communication with the exhaust lumen 132.

Because the liquid exhaust trap 130 may function as a heatsink, the trap 130 may be fabricated from a thermally conductive material which also has a relatively large heat capacity, e.g., aluminum, copper, or other metals. In other variations, plastics such as polycarbonate (which generally have heat capacities greater than metals such as aluminum but relatively lower thermal conductivity values) may also be utilized for fabricating the liquid exhaust trap 130. Other factors such as weight and manufacturing processes are further considerations in designing the liquid exhaust trap 130. Additionally, a fan may also be incorporated into the liquid exhaust trap 130 to facilitate thermal energy exchange with the environment. During use, as the discharged cryoablative agent from the liner 20 passes through the exhaust line 98 and into the fluid trap 134 portion of liquid exhaust trap 130, any liquid 136 form of the cryoablative agent may collect within the fluid trap 134 while the gaseous form may continue to be vented through the exhaust lumen 132 and out through the evacuating exhaust line 140. The captured liquid 136 may be subsequently warmed enough by contact with the liquid exhaust trap 130 to turn into a gaseous form for venting through the exhaust lumen 132.

Additionally and/or alternatively with respect to the liquid exhaust trap 130, the evacuating exhaust line 140 may form a length of tubing, e.g., 5 ft., which may optionally be convoluted in configuration and which could be used to provide sufficient surface area and a pathway to facilitate heat exchange with the environment and promote the evaporation of any liquid cryoablative agent.

Figure 7A:
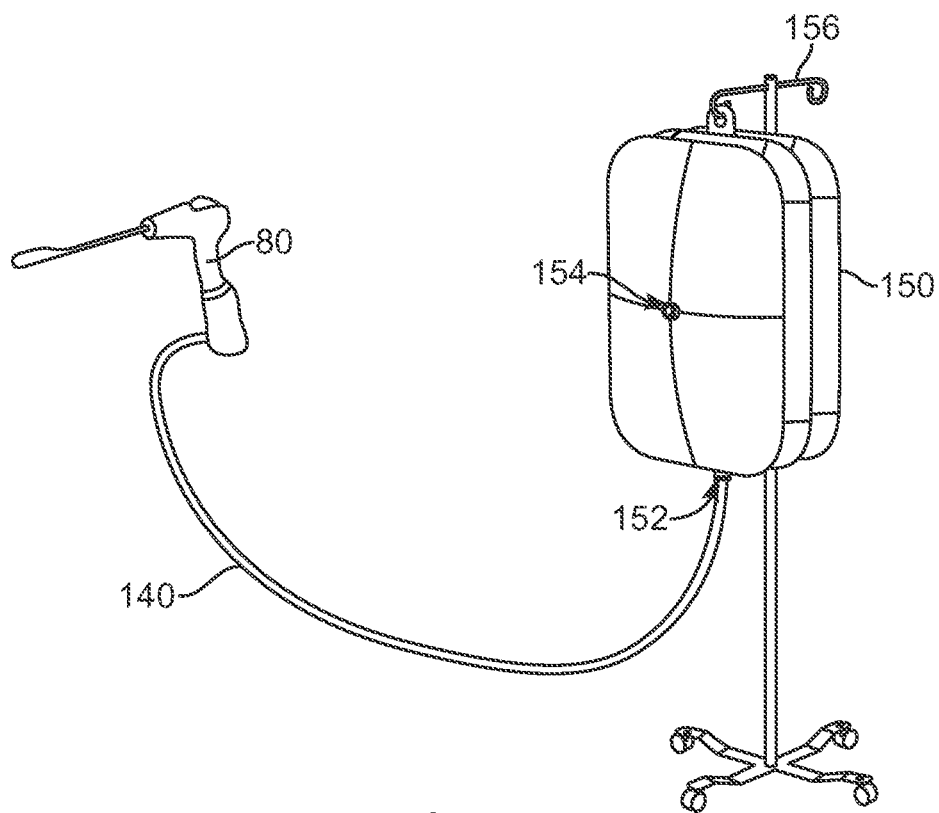
FIGS. 7A and 7B show examples of collection systems which can be used to collect the discharged liquid or gas.
Figure 7B:
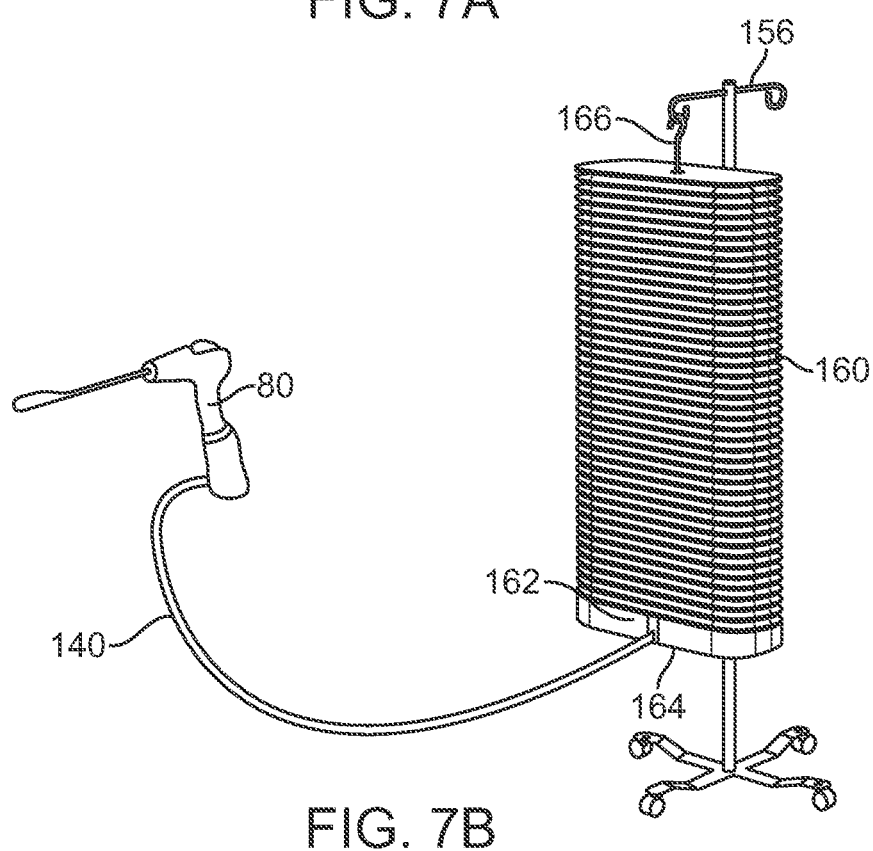

With the discharged cryoablative agent in a completely gaseous state, the evacuating exhaust line 140 may be vented to the surrounding environment or optionally coupled to a scavenging system to collect the discharged gas to limit exposure. FIGS. 7A and 7B show assembly views of examples of collection bags which may be optionally used with the treatment assembly. Scavenging systems may incorporate features such as orifices or valves to prevent any vacuum applied by the scavenging unit from interfering with the backpressure within the treatment device.

FIG. 7A shows an inflating collection bag 150 which is expandable in width coupled to the evacuating exhaust line 140 via a disconnect valve 152 (e.g., unidirectional valve). The collection bag 150, which may be reusable or disposable, may be supported via a pole 156 and may also incorporate a release plug 154 which may allow for the venting of the collected gas during or after a treatment procedure is completed.

Similarly, FIG. 7B shows an accordion-type collector 160 also supported via a pole 156 and a connector 166 attached to the collector 160. The evacuating exhaust line 140 may be removably coupled to the collector 160 via a disconnect valve 162 (e.g., unidirectional valve) and may also incorporate a release plug 164 for venting any collected gas during or after a treatment procedure. The vertically-expanding collector 160 may define a hollow passageway through the center of the vertical bellows which allows for the connector 166 (e.g., rigid rod or flexible cord) to pass through and support the base of the collector 160. The connector 166 also prevents the collector 160 from falling over to a side when inflating. As the gas enters through the bottom of the collector 160, the bellow may inflate upward.

Inflow and Venting Control

Figure 8:
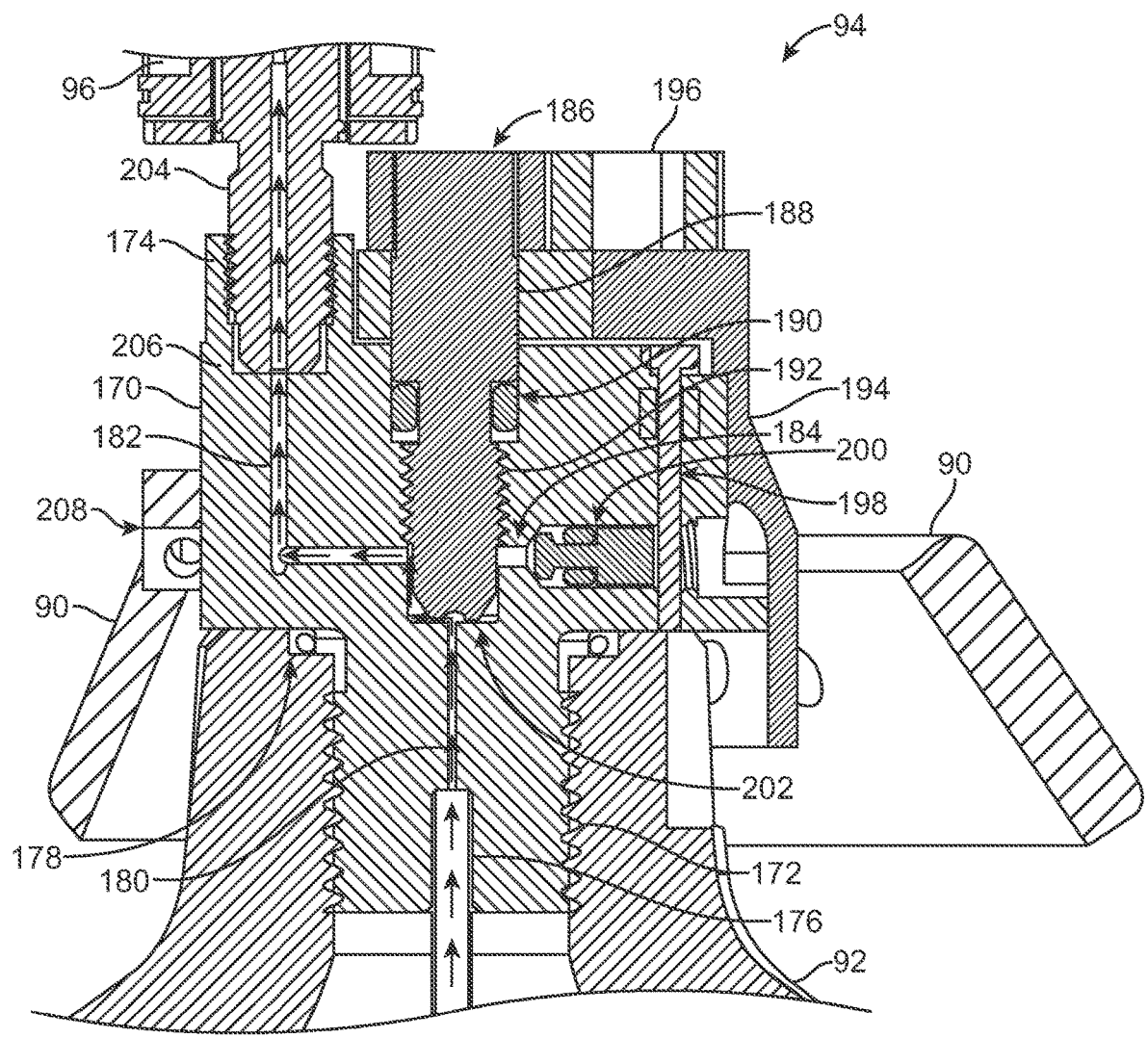
FIG. 8 shows a cross-sectional side view of a cylinder valve which may be integrated with the handle of the assembly.

In further controlling the flow of the cryoablative agent within the treatment assembly, the reservoir or canister valve 94 which is coupled directly to the reservoir or canister 92 may also incorporate a number of flow control features. FIG. 8 shows a cross-sectional side view of one variation of the reservoir or canister valve 94 which may include an integrated reservoir lumen insert 176 extending from the reservoir interface 172 for direct insertion into the reservoir or canister 92 to facilitate the transfer of the liquid cryoablative agent through the valve 94 and into the treatment assembly. A reservoir seal 178 may be incorporated to ensure a fluid tight seal between the reservoir or canister 92 and the reservoir interface 172. The valve 94 may include a valve body 170 which defined pathways for normal fluid flow as well as a venting pathway for emptying of the reservoir or canister 92.

The valve body 170 may have the reservoir interface 172 extending from the body 170 for secure engagement with the reservoir or canister 92 (e.g., via a threaded engagement). The valve body 170 may further include a modulation control interface 174 which defines an interface seal 206 for securely coupling (e.g., via a threaded engagement) with a modulation control coupler 204 extending from the inflow modulation control unit 96. A valve stem 186 may be seated within a valve stem channel 188 defined within the valve body 170. The valve stem 186 may be secured to the valve body 170 via a threaded engagement 192 and a valve stem seal 190 which ensures a fluid-tight connection between the two components. The valve stem 186 may be attached to a valve stem coupler 196 which is connected to the reservoir engagement control 90 via a control member 194.

During use, the reservoir engagement control 90 may be rotated (e.g., about 45 degrees) about the reservoir housing 88 and/or the handle 84. This in turn may rotate the control member 194 and valve stem coupler 196 which further rotates the valve stem 186 relative to the valve body 170 and opens the valve stem seal 202. The opened valve stem seal 202 then enables the flow of the cryoablative agent into the reservoir lumen insert 176 and into the proximal inflow lumen 180 located proximal to the valve stem 186, past the opened valve stem 186, and into the distal inflow lumen 182 for further passage into the inflow modulation control unit 96.

Actuation of the reservoir engagement control 90, control member 194, and/or valve stem coupler 196 may optionally send an electrical signal to the microprocessor or controller 110 that the treatment assembly 80 is charged with the cryoablative agent and ready for a treatment procedure. Once the treatment procedure is completed and the inflow modulation control unit 96 has been optionally closed to any further inflow of the cryoablative agent, a vent pin 198 may be actuated or pulled relative to the valve body 170 to release a vent piston 200. With the vent pin 198 secured in the valve body 170, the vent piston 200 may seal a venting lumen 184 but with the vent pin 198 removed, the vent piston 200 may freely translate relative to the valve body 170 thus allowing any remaining cryoablative agent within the reservoir or canister 92 to vent through the venting lumen 184 (with the valve stem 186 still in its open position) and into the environment or into a collection reservoir, as described herein.

Additionally, a pressure relief mechanism 208 may be optionally incorporated into the valve body 170 to function as a burst valve or other pressure release mechanism for safety purposes.

Figure 9:
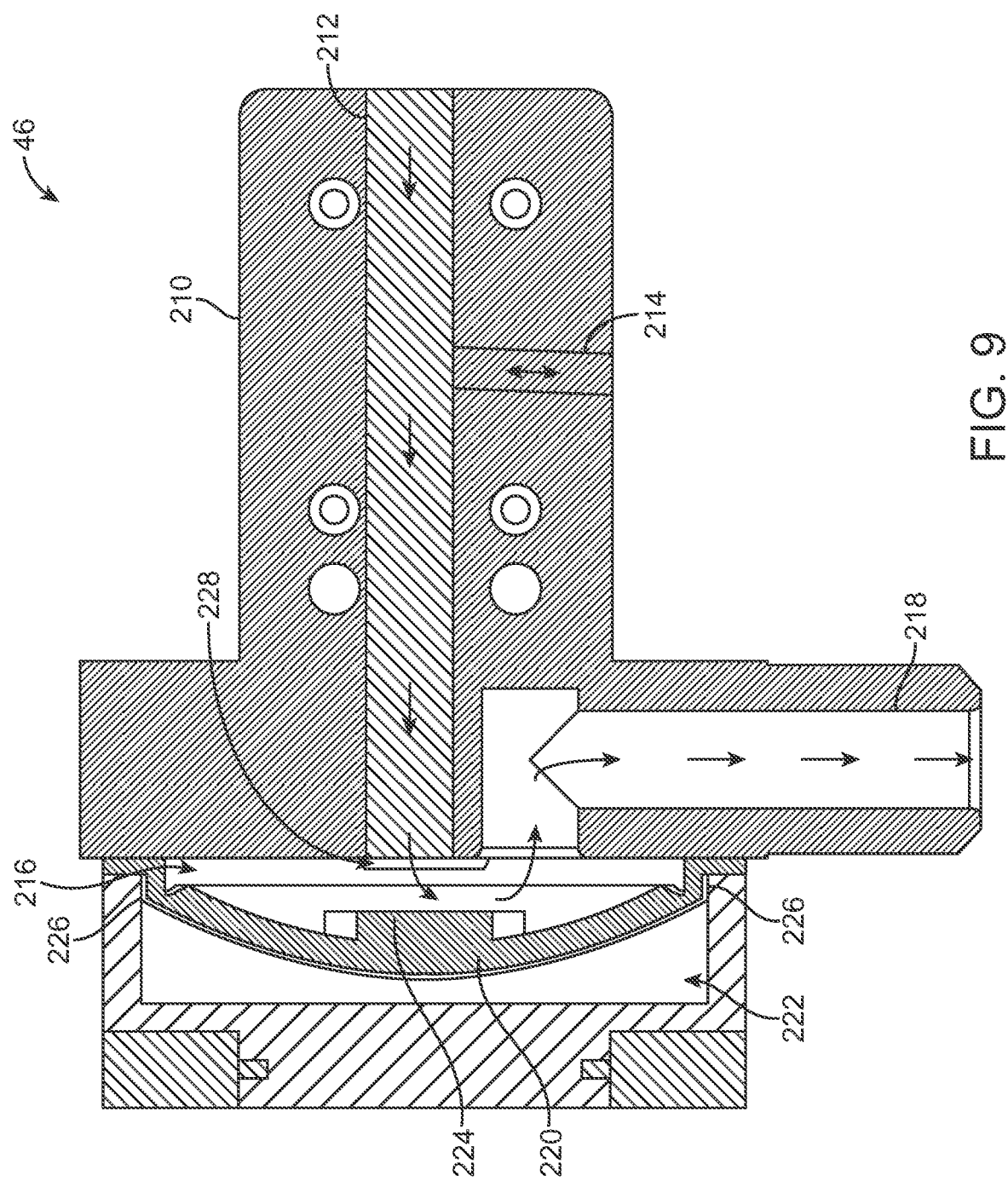
FIG. 9 shows a cross-sectional side view of an actuatable exhaust valve which may be integrated with the handle of the assembly.

Yet another feature which may be optionally incorporated into the treatment assembly for opening and closing the exhaust gas pathway to facilitate gradual pressurization of the liner and uterine cavity with filtered air as well as the application of vacuum to the liner and uterine cavity following the infusion of the cryoablative fluid may be seen in the partial cross-sectional side view of FIG. 9 which illustrates an actuatable dome-shaped valve located within the exhaust block 46 at a proximal end of the sheath 12. The exhaust block 46 may comprise in part a body 210 which defines an exhaust lumen 212 in fluid communication with the interior of the liner 20. The exhaust lumen 212 may also be in fluid communication with a pump/vacuum lumen 214 which provides a channel for air for the initial inflation of the liner 20 against the tissue surface prior to infusion of the cryoablative agent.

Although shown and described as a dome-shaped valve, such a valve is one of a variety of pneumatic and/or electro-mechanical valves that may be used to open and close the exhaust gas pathway in the assembly described herein. The valve may generally comprise a dome-shaped flexible member 220 attached at its periphery to the body 210 via attachment 226. The flexible member 220 may further include a seal 224 which extends from a central portion of the concave surface of the flexible member 220. The flexible member 220 may be located within a pressurization chamber 222 which normally exerts a pressure which is less than a deflection force required to collapse the flexible member 220. When the treatment assembly is used to initially puff the liner 20 with air to force the liner 20 into contact with the surrounding tissue, the air may pass through the pump/vacuum lumen 214 and into the interior of the liner 20. The air within the pressurization chamber 222 may also be pressurized by the same pump such that the pressure increase collapses the flexible member 220 and forces the seal 224 into contact against a corresponding sealing lip 228 located at an opening of the exhaust lumen 212 adjacent to the seal 224.

When the initial pressurization of the liner 20 has been completed, the air may be removed by releasing the pressure within the pressurization chamber 222 allowing the flexible member 220 to reconfigure into its opened domed shape and to release the seal 224 from the sealing lip 228. This may then allow for the exhaust from the liner interior to flow through the exhaust lumen 212, through an exhaust chamber 216, and further into an exhaust lumen 218 for venting from the treatment assembly, as described herein.

Liner Removal

In further facilitating a treatment procedure, the liner may also be configured to aid in its removal from the underlying tissue after a cryoablation treatment. After the tissue has been treated, the liner 20 may remain frozen on the underlying uterine tissue preventing removal of the liner 20 from the patient's body for up to several minutes. The liner 20 may be left in the patient for a period of time after the cryoablation treatment until the tissue thaws as pulling the liner 20 from the tissue prematurely may tear the liner 20; however, leaving the liner 20 in place may increase patient discomfort. Hence, to facilitate removal of the liner 20 from the underlying frozen tissue, a number of different warming techniques may be optionally implemented.

Circulating a warm or room temperature fluid within the liner is one method for thawing the liner 20 and adjacent tissue to expedite the removal of the liner 20. A gas (e.g., air, expanded helium, etc.) may be used instead of a liquid as a warming gas may prevent the creation of a solid which could potentially block the exhaust gas pathway. Additionally, use of a warming gas may also slow the boiling-off of any remaining cryoablative liquid as boiling-off the cryoablative liquid too quickly could create a pressure spike within the liner 20. A liquid with a freezing point lower than the boiling point of the cryoablative agent, such as nitrous oxide, may be utilized but may not be required. It may also be possible to use a liquid which has a much higher boiling point than the cryoablative fluid provided that all of the cryoablative fluid has previously boiled-off. Closing the actuatable valve within the exhaust block and measuring the pressure inside the liner is one way to detect if any of the cryoablative fluid remains: an increase in pressure would indicate the presence of liquid cryoablative fluid still boiling-off.

Figure 10:
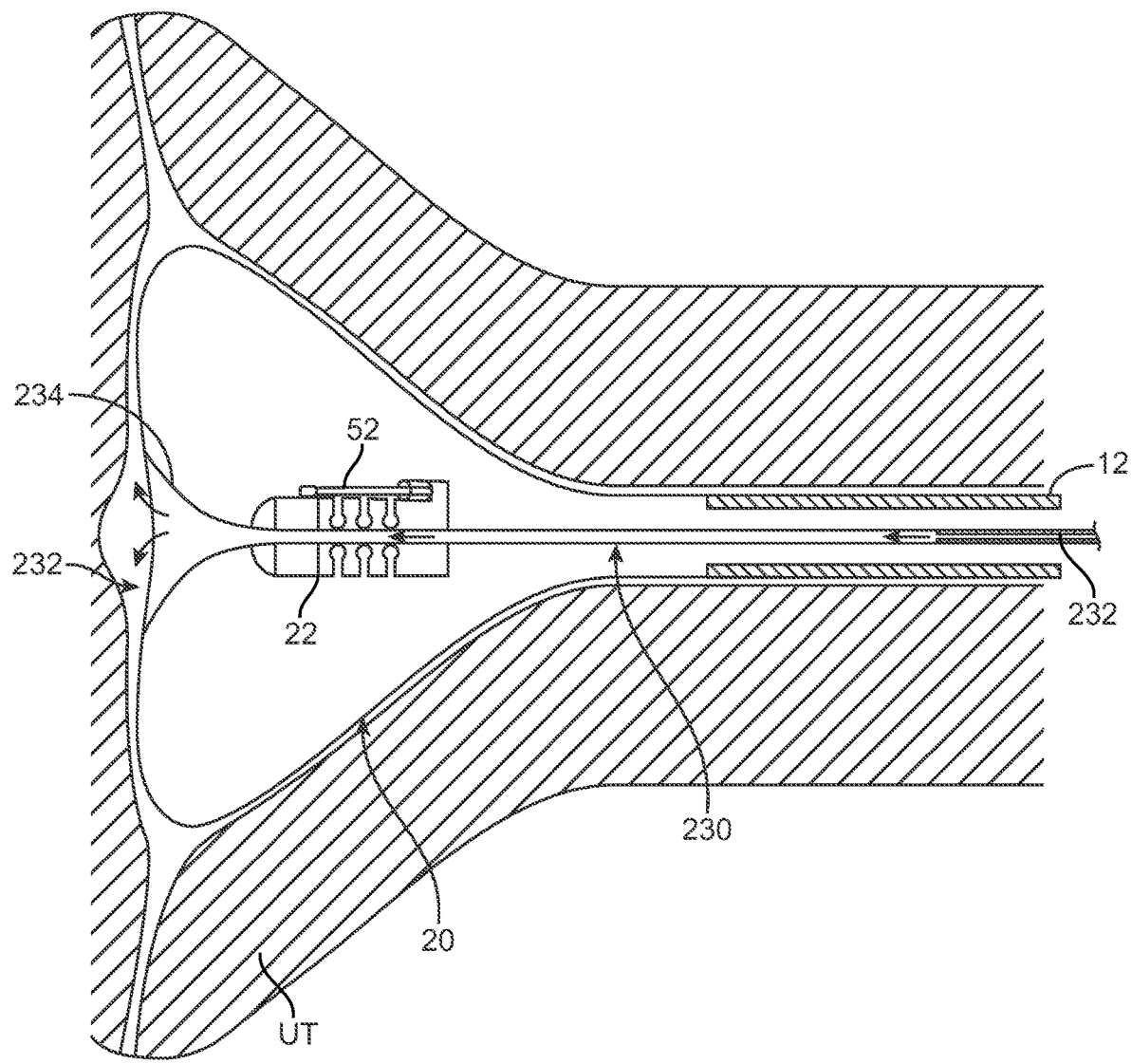
FIG. 10 shows a partial cross-sectional view of a liner having an integrated lumen for introducing a warming liquid or gas to facilitate liner removal.

One variation is shown in the partial cross-sectional top view of FIG. 10 which shows a liner having a warming fluid lumen 230 integrated with the liner 20 and cooling probe 22. The warming fluid lumen 230 may be formed integrally with the distal portion of the liner 20 and extend proximally through the interior of the liner 20 and/or cooling probe 22. During the cryoablation treatment procedure, the warming fluid lumen 230 may remain in a flattened configuration which is non-obstructive to the introduced cryoablative agent. However, once the cryoablation treatment has been completed and the liner 20 is to be removed from the uterus UT, a fluid 232 (e.g., saline, water, etc.) which may be warmed may be introduced into the warming fluid lumen 230 from outside the patient body such that the fluid 232 flows through the lumen 230 and the liner 20 interior and out the distal portion of liner 20 through a lumen opening 234 and into direct contact against the tissue surface and the exterior of the liner 20. The fluid 232 may warm the contacted frozen tissue and facilitate the release of the liner 20 from the tissue surface as the fluid 232 pushes the liner 20 away from the frozen tissue. The fluid 232 may be introduced continuously or intermittently (e.g., via a syringe, pump, or by the treatment assembly itself) while the liner 20 is retracted from the uterus UT and out of the patient body. For fluid circulation external to the liner 20, a liquid may be used over a gas because of the relatively higher heat transfer rate which is possible with a liquid.

Figure 11A:
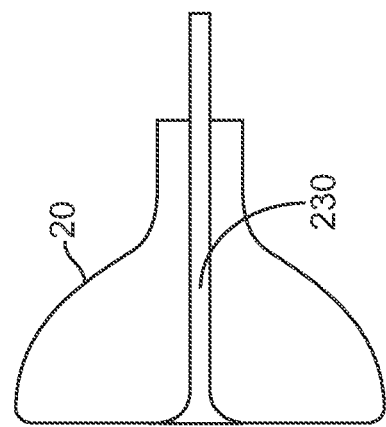
FIGS. 11A and 11B show an example for fabricating the liner having the integrated lumen.
Figure 11B:
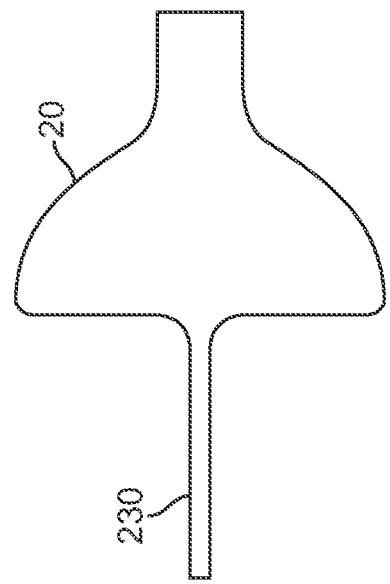

FIGS. 11A and 11B illustrate one variation for fabricating the liner 20 with an integrated fluid lumen 230. The liner 20 may first be formed to include a lumen 230 which protrudes distally from the distal end of the liner 20, as shown in the top view of FIG. 11A. Once such a liner has been formed, e.g., via RF welding, the fluid lumen 230 may be inverted such that it passes through the interior of the liner 20, as shown in the top view of FIG. 11B. This variation illustrates one example for incorporating a fluid lumen with the liner 20; however, any number of other methods may be utilized as well.

Figure 12A:
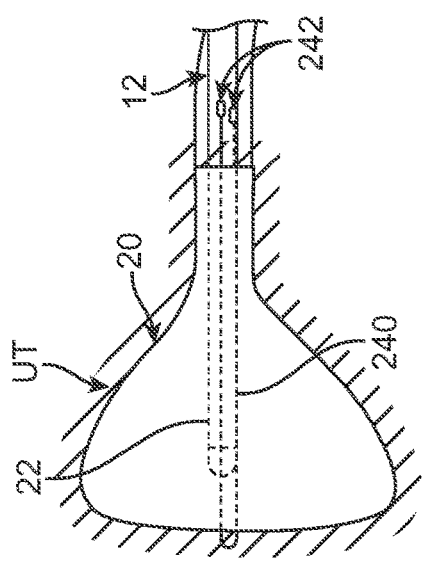
FIGS. 12A and 12B show respective top and side views of a liner having an integrated tether or wire for facilitating liner removal.
Figure 12B:
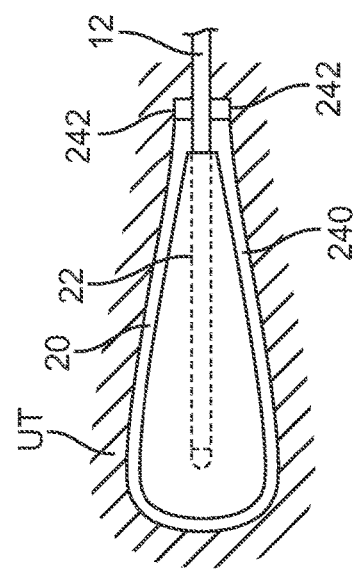

Aside from forming an integrated fluid lumen into the liner, other mechanisms may instead be utilized to facilitate liner removal from the contacted tissue. FIGS. 12A and 12B illustrate top and side views, respectively, another variation of a liner 20 incorporating a tether or wire 240 (e.g., Kevlar, Nylon, etc.) which may be positioned externally of the liner 20 such that it lies between the surrounding tissue and liner exterior. Initially, the tether or wire 240 may be loosely looped over the liner 20 to prevent any interference from the tether or wire 240 for liner deployment. Alternatively, the tether or wire 240 may be integrally formed with the liner 20 material itself or the tether or wire 240 may be attached along the interior surface of the liner 20. In either case, the tether or wire 240 may be attached at shaft attachment points 242 while extending over the entire length of the liner 20 when deployed against the tissue.

Figure 13A:
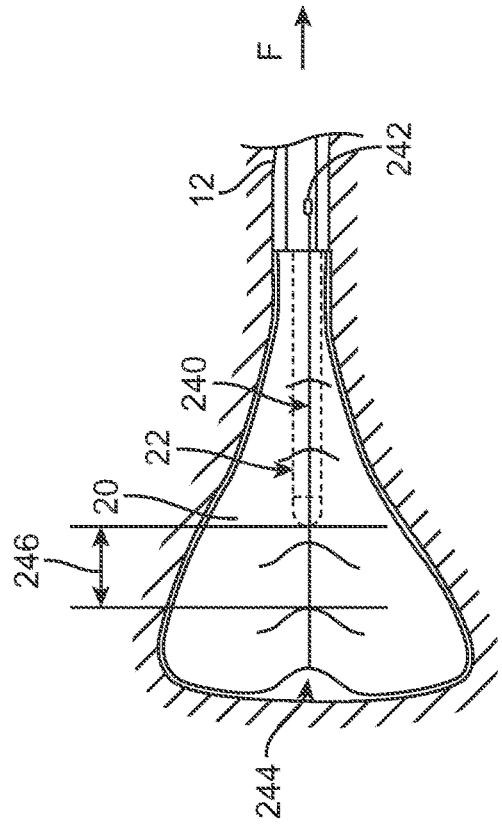
FIGS. 13A and 13B show respective top and side views of the tether being tensioned and the release of the liner from the tissue surface.
Figure 13B:
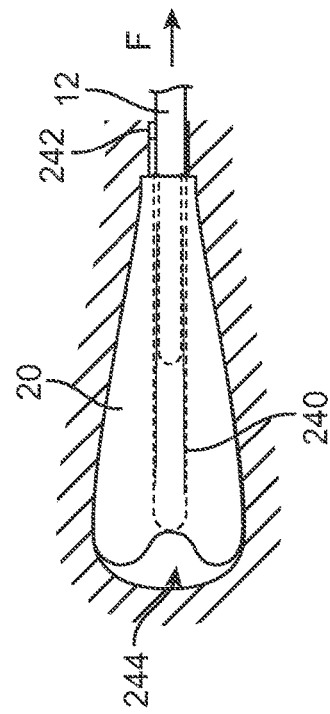

Once the liner is ready to be removed from the uterine tissue, the tether or wire 240 may be tensioned either via a control mechanism on the device handle or via simply pulling on the device. The variation shown in the top and side views of FIGS. 13A and 13B illustrate how retraction of the sheath 12 may tension the tether or wire 240 such that the liner 20 may begin to pull away 244 from the tissue. The presence of the tether or wire 240 may help to ensure that the liner 20 remains attached to the treatment assembly. The distance 246 that the liner 20 has stretched during sheath retraction 12 may be seen in FIG. 13A. The tether or wire 240 may continue to be tensioned until the liner 20 has pulled entirely from the tissue surface.

Figure 14:
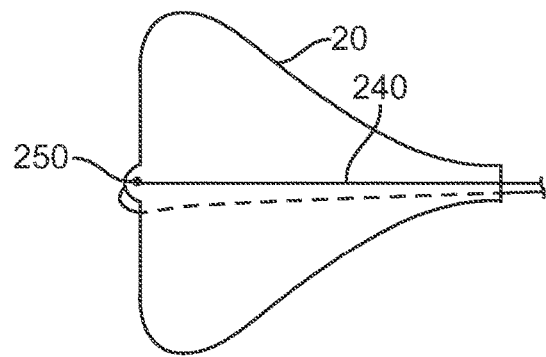
FIG. 14 shows a top view of another variation of the liner having a tether or wire extending through a guide hole defined through a tab on the exterior of the liner.

In yet another variation, FIG. 14 shows a top view of a liner 20 which may incorporate a guide hole 250 at a distal end region of the liner 20. The tether or wire 240 may pass externally of the liner 20 into and through the guide hole 250 such that the tether or wire 240 may remain looped around the liner exterior.

Figure 15:
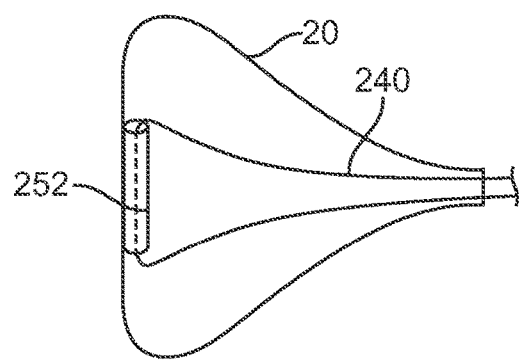
FIG. 15 shows a top view of yet another variation of the liner having a tether or wire extending through a channel defined along the liner.

FIG. 15 shows yet another variation where a guide tube 252 may be integrally formed with the liner material either externally or internally of the liner 20. The guide tube 252 may extend laterally along the distal portion of the liner 20 such that the tether or wire 240 may be looped securely through the guide tube 252.

Figure 16:
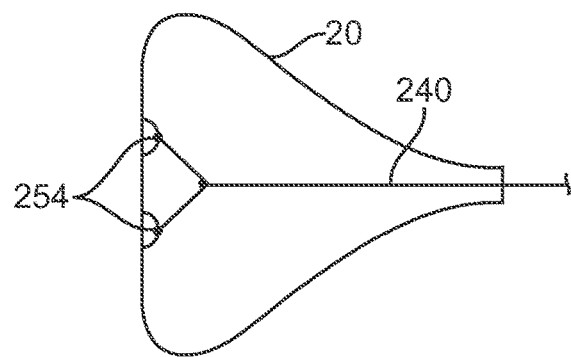
FIG. 16 shows a top view of yet another variation of the liner having a tether or wire extending through several guide holes.

FIG. 16 shows yet another variation where two or more guide holes 254 may be formed along the interior of the liner 20. The tether or wire 240 may be attached to a secondary tether or directly to each of the guide holes 254.

Figure 17:
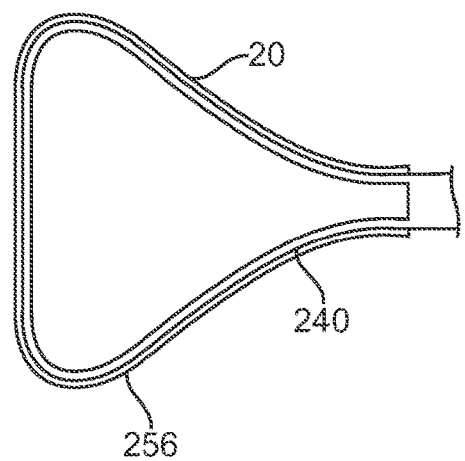
FIG. 17 shows a top view of yet another variation of the liner having a tether or wire extending around a periphery of the liner.

FIG. 17 shows yet another variation where a peripheral channel 256 may be formed around the periphery of the liner 20 such that the tether or wire 240 extends through the peripheral channel 256 entirely around the liner 20.

Figure 18:
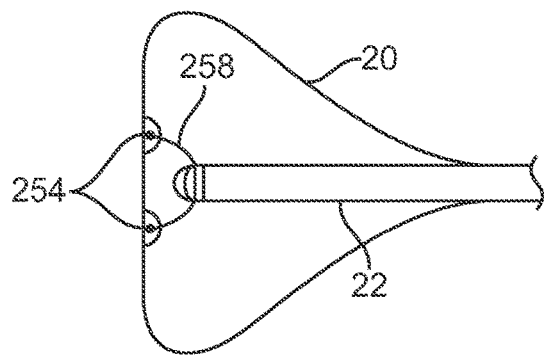
FIG. 18 shows a top view of yet another variation of the liner having a tether or wire coupled to a distal end of the exhaust tubing.

FIG. 18 shows yet another variation where the two or more guide holes 254 formed along the liner interior with a tether 258 extending between the holes 254 may also be attached to the probe 22. Retraction of the probe 22 may tension the distal end of the liner 20 to facilitate its release from the tissue.

In these examples and any of the variations herein, a wire or heating element which may be warmed or energized (e.g., infrared) may be located on the probe shaft or positioned within the liner 20 interior. Once the treatment procedure has been completed, the wire or heating element may be activated to warm the liner 20 and the adjacent contacted tissue to facilitate the thawing of the tissue for removal of the liner 20.

Additionally and/or alternatively, the liner 20 may be comprised of a lubricious liner or a separate non-stick coating may be applied to the liner exterior. It is not uncommon for polymers such as urethanes, especially thin films, to stick together if tightly-packed during sterilization, transportation and storage. The liner 20, being a thin polyurethane film compressed into a sheath, may employ a lubricious material or surface to ensure that the liner 20 fully deploys and inflates following unsheathing. For instance, the lubricity of the liner 20 may be increased through the formulation of the urethane blend used to make the thin film. Diatomaceous earth may also be utilized as an additive to the liner material to make the surface irregular to prevent the film from sticking to itself. Lubricants can also be added to the interior and/or exterior of the liner 20 to increase its lubricity and prevent the liner from sticking to itself after being sheathed. Silicone oil and talc are examples of two possible lubricants. Surface lubricants can also be applied to the film before or after the liner is RF-welded.

Another method for preventing the liner from sticking to itself is to keep the liner 20 unsheathed until just prior to delivery and deployment. A simple liner folding tool can be included within the sterile package to enable the user to easily load the liner 20 into the sheath in its pleated configuration. In order to prevent the device from being used prior to the sheath being advanced over the liner 20, the position of the sheath may be used as an input in a system check algorithm.

Figure 19:
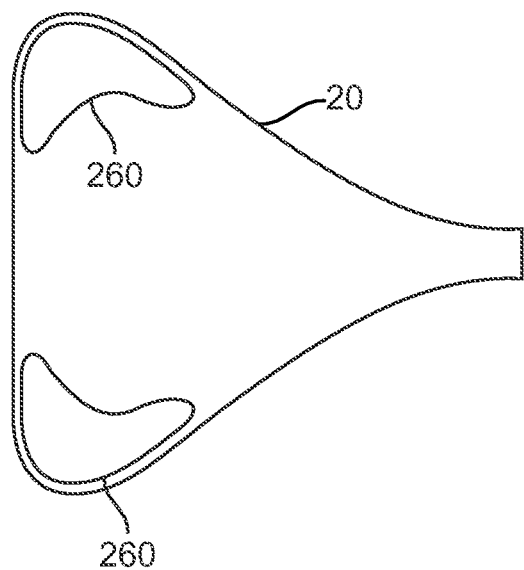
FIG. 19 shows a top view of another variation of the liner having insulated regions defined along one or both sides of the liner.

Because optimal ablation coverage and depths may not be uniform over the entire contacted tissue region, the liner 20 may be adjusted in thickness over particular regions of the liner 20 to insulate predetermined tissue regions to result in tailored ablations. Ablation depths may be shallower where the liner 20 is relatively thicker due to less efficient thermal transfer across the thicker areas. One example is shown in the top view of FIG. 19 which illustrates the liner 20 having insulated regions 260 of the liner (e.g., thicknesses greater than 0.0012 in.), for instance, near the distal portions of the liner such as near the uterine cornua and lower segment when the liner 20 is deployed within a uterine cavity. Alternatively, multiple layers of the membrane may be utilized where liner thickness is to be increased. Having the thickened regions 260 insulate the contacted tissue may help to prevent intrauterine adhesions. Another variation may include a liner 20 having, for instance, quilted pockets filled with air or gas to insulate targeted regions and reduce ablation depth and possibly even coverage.

Figure 20:
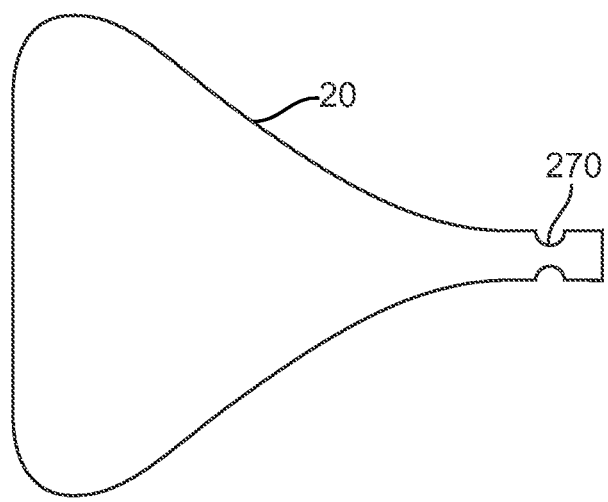
FIG. 20 shows a top view of another variation of the liner having regions configured to have predetermined weakened areas.

In yet another variation, the liner 20 may be designed with one or more predetermined weak points, as shown in the top view of FIG. 20. If excessive tension were applied to the liner 20 while it is frozen to tissue, the liner 20 could tear. By locating one or more weakened regions 270 of the liner 20 near, e.g., the proximal connection to the probe shaft, the liner 20 may be designed to tear specifically at the designated weakened regions 270 which may make retrieval of the detached liner 20 as a single piece relatively easier once the tissue fully thaws. It is preferable that the liner 20 remain intact when tension is applied during the removal of the device from the patient body. However, it may be advantageous to have designated weakened regions 270 to prevent too much force from being applied to the uterine tissue. The location of the weakened regions 270 may also be chosen to facilitate removal of the liner 20 as a single piece after the uterus has warmed following a cryotherapy treatment.

Figure 21:
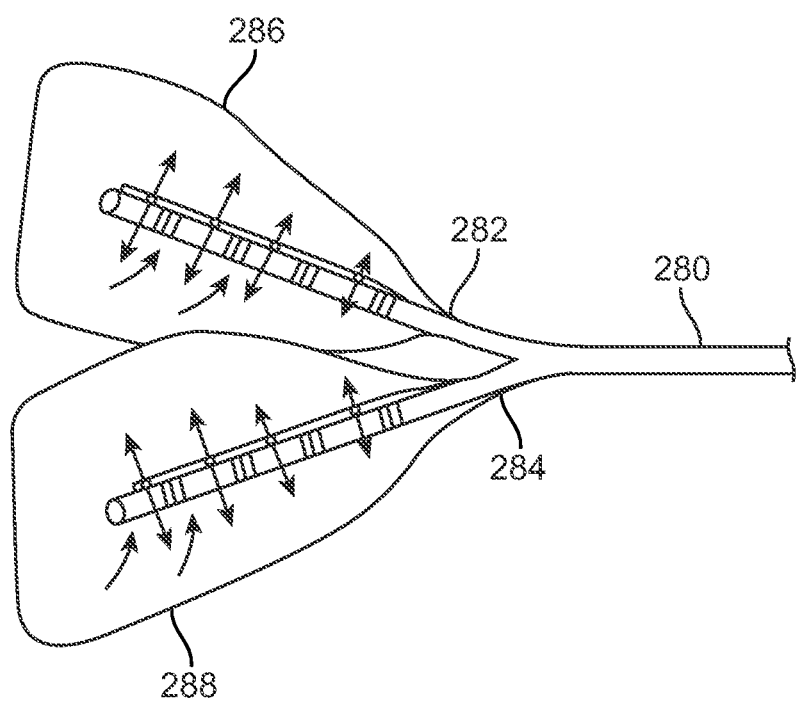
FIG. 21 shows a top view of another variation of the assembly having multiple liners.

In yet another variation of the liner, the liner may be separated into several individual liners in a multi-liner assembly, as shown in the variation of FIG. 21. Because it is not uncommon for uterine cavities to be arcuate, septate, bicornuate or have other abnormalities, the liner may be configured to have two more liners which could be deployed simultaneously. Such a multi-liner probe may deliver different cryotherapy or hyperthermic therapies to different parts of the uterus, if so desired. In the variation shown, a single probe shaft 280 may include a first cooling probe 282 and a second cooling probe 284 extending at an angle from the probe shaft 280. The cooling probes 282, 284 may each have a respective first liner 286 and second liner 288 where each liner may be deployed to function in the same manner as described herein. Moreover, while two separate liners are shown, other variations may include more than two individual liners depending upon the desired treatment results.

Probe Control

Figure 22A:
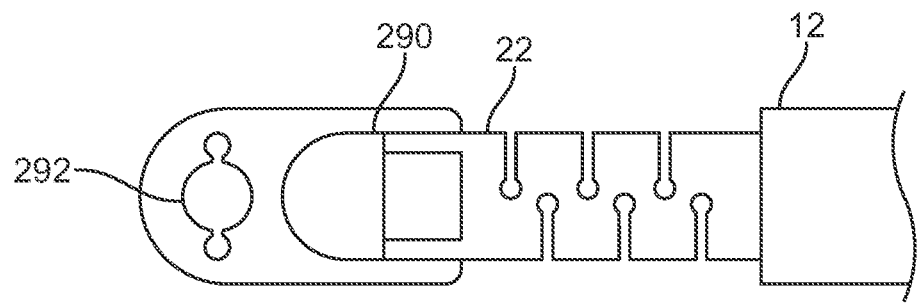
FIGS. 22A and 22B show top views of another variation of the cooling probe having a compressible tip to present an atraumatic surface to the liner interior and tissue surface.
Figure 22B:
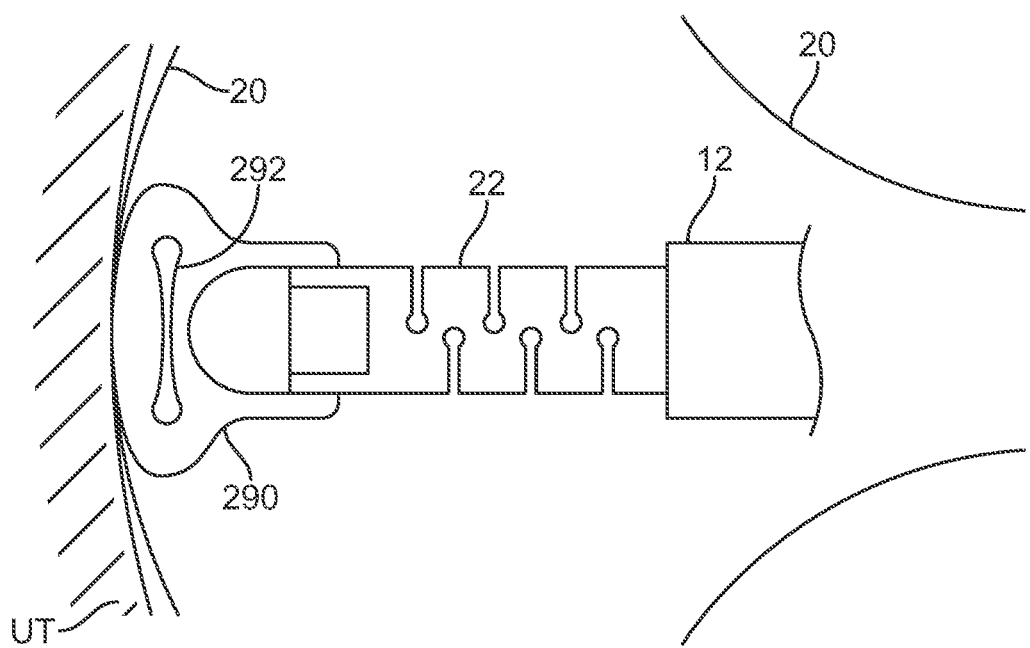

In any of the variations described herein, the cooling probe 22 may optionally include a compressible tip 290 having a collapsible opening 292 defined through the tip 290, as shown in the top view of FIG. 22A. The compressible tip 290 may be positioned upon the distal tip of the probe 22 located within the interior of the liner 20. Because the probe 22 may be translatable within the liner 20 and relative to the sheath 12, the tip 290 may present a soft and atraumatic surface in the event the probe 22 is advanced into contact against the interior of the liner 20 and underlying tissue surface, as shown in FIG. 22B, to prevent liner tears or trauma to the uterine tissue UT. If the tip 290 is compressed against the liner 20 and/or tissue, the opening 292 may expand laterally to increase in diameter. In alternative variations, any number of relatively soft materials which can withstand the temperature of the cryoablative agent may be utilized and other shapes and structures may also be utilized.

Aside from the tip contacting the interior of the liner 20, the cooling probe 22 itself may become inadvertently buried or urged into the anterior or posterior tissue surface of the uterus UT when deployed within the uterine cavity. This is due to the orientation of the uterus UT which is typically angled relative to the vaginal opening of the patient (anteverted or retroverted) as well as along the body of the uterus UT itself (anteflexed or retroflexed), as shown in the cross-sectional side view of FIG. 23. With the sheath 12 introduced through the cervix CV and retracted and the liner 20 deployed and expanded into contact within the uterine cavity, the cooling probe 22' may have a tendency to be urged into the posterior tissue wall of the uterine cavity when advanced or adjusted into position within the liner interior, as illustrated. However, the cooling probe 22 is preferably located at a central position within the expanded liner interior, as illustrated, in order to allow for the uninhibited infusion of the cryoablative fluid from the infusion line 52. Having the probe 22 placed directly against the liner interior and underlying tissue wall may obstruct the infusion line 52 potentially resulting in an uneven ablation pattern in the tissue.

Hence, the cooling probe 22 may be fabricated from a material such as annealed stainless steel which may provide the probe 22 with improved ductility due to its minimized internal stresses. This improved ductility allows for the probe 22 to flex relative to the sheath 12 away from the walls of the liner interior and contacted tissue walls such that the probe 22 may be centered within the expanded liner 20 particularly in the reduced temperature environment during cryoablation. The use of fully annealed stainless steel may facilitate the positioning of the probe 22 within the liner 20 due in part to the slots defined along the probe 22 but also due to the material properties. For instance, the probe 22 fabricated from annealed stainless steel may have, e.g., a 0.006 in. wall thickness, selected to minimize overall device diameter while maintaining sufficient hoop-strength to prevent it from being crushed or kinked in-use. Annealing the slotted stainless steel exhaust tube may also improve its cyclic fatigue life compared to a half-hard or a full-hard material.

In yet other variations, rather than utilizing annealed stainless steel, other shape set materials may be used. For instance, a simple steel cannula or a more complex articulating cannula which may incorporate multiple individual elements which are flexible in a first state and optionally locked into a particular configuration in a second state may also be used although not necessary. However, it is desirable that the cannula takes the shape of the uterine cavity within the sagittal plane of the patient and uterus UT without being biased to either the anterior or posterior side of the uterus UT. Provided that the cannula flexes with the shape of the uterus UT, holds its flexed position during the cryoablation treatment, and also has substantial radial strength to prevent crushing and/or kinking of its shape, any number of shape set materials may be utilized.

Reservoir Temperature Control

During a cryotherapy treatment, it is desirable to control the amount of the cryoablative agent delivered into and through the liner 20. A few of the parameters which may affect the flow rate and volume of the cryoablative agent discharged from the reservoir or canister 92 may include temperature of the treatment assembly 80 and reservoir or canister 92 as well as ambient temperature in which the assembly 80 is used as such temperatures can affect the internal pressure of the reservoir or canister 92. Unless controlled by other methods, the flow rate of a pressurized cryogen is generally controlled by the internal pressure of the vessel in which the cryoablative agent is contained. Thus, in order to be able to deliver a consistent cryoablative therapy over a range of device and room temperatures, controlling either the inflow rate or starting temperature and pressure of the cryogen is desirable.

One method for controlling the starting cryogen pressure is by designing the system to operate at the high end of the temperature range and heating the reservoir or canister 92 to a specified temperature and corresponding internal pressure. The heat could be supplied by a various mechanisms such as an electrical heating element wrapped around the reservoir or canister 92. In one variation, the electrical power for the heating element could be provided by a battery within the device itself.

Figure 24:
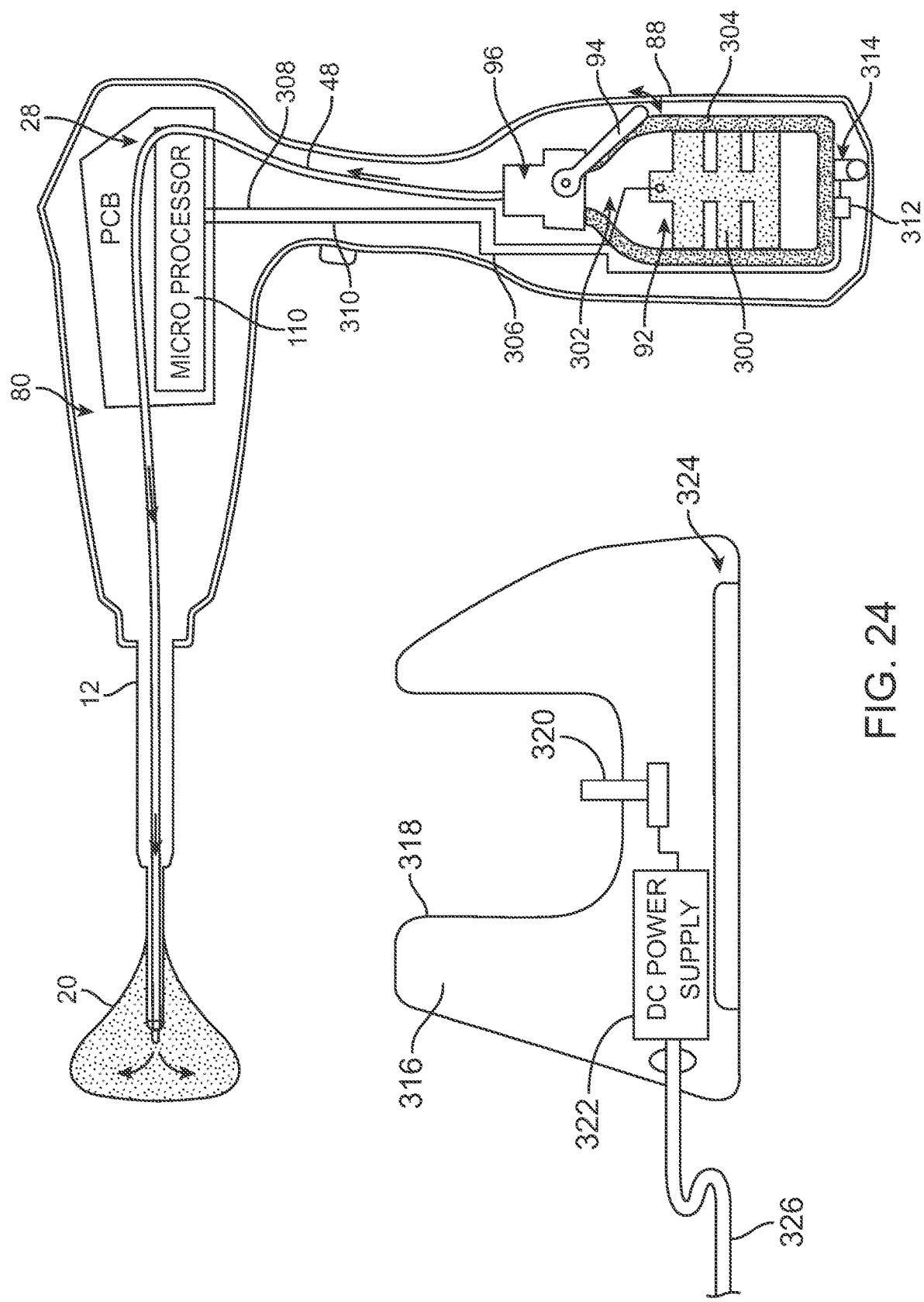
FIG. 24 shows a schematic illustration of a treatment assembly optionally including a temperature controlled cradle.

In another variation, the electrical power may be provided by a heating cradle 316 prior to device use, as shown in the exemplary schematic side view of FIG. 24. A separate warming cradle 316 may define a receiving channel 318 sized to receive the reservoir housing 88 of the treatment assembly 80. The cradle 316 may further include an electrical connector 320 connected to an optional power supply (DC) 322 (which may be recharged) and/or the cradle 316 may be electrically connected to a stationary power supply via a power supply (AC) line 326. The cradle 316 may also incorporate an optional stabilizing weight 324 to provide for stability when the treatment assembly 80 is docked within the receiving channel 318.

The treatment assembly 80 itself may incorporate a heating element 300 (e.g., a resistive heating element) which may be wrapped partially or entirely around the reservoir or canister 92. A layer of insulation 304 may also be provided around the reservoir or canister 92 to provide for a thermally stabilized warming environment. A temperature sensor 302 (e.g., thermocouple, thermistor, etc.) may also be incorporated for thermal contact with the reservoir or canister 92 for sensing the canister temperature. An electrical connector 314 may be located correspondingly along the reservoir housing 88 for electrically contacting the electrical connector 320 positioned upon the cradle 316 such that the cradle 316 may provide electrical power to the treatment assembly 80 when docked within the cradle receiving channel 318.

A connection sensor 312 may be electrically connected to the connector 314 such that the sensor 312 may provide a signal via connection line 310 to the microprocessor or controller 110 indicating that the treatment assembly 80 has been docked and is able to receive power from the cradle 316. The heating element 300 may also be electrically coupled to the microprocessor or controller 110 via heating element line 306 and the temperature sensor 302 may likewise be coupled to the microprocessor or controller 110 via temperature sensor line 308.

With the heating element 300 and temperature sensor 302 so coupled to the microprocessor or controller 110, the heating assembly may form a closed-loop system where the microprocessor or controller 110 may be programmed via a software algorithm to control the electrical power supplied to the heating element 300 depending upon the measured temperature of the temperature sensor 302 such that the reservoir or canister 92 is heated to a predetermined temperature or maintained within a predetermined temperature range prior to a cryotherapy treatment. The insulation 304 may accordingly slow the rate of cooling of the reservoir or canister 92 and also extend the available time between the removal of the treatment assembly 80 from the cradle 316 and the initiation of the treatment.

The microprocessor or controller 110 may be further programmed to alert or indicate (e.g., auditory or visual) to the user that the treatment should be initiated before the sensed temperature (and pressure) of the reservoir or canister 92 drops below a set point temperature desired for completion of a full cryotherapy treatment. An auditory and/or visual indicator (e.g., lights, alarms, or other visual or auditory cues) may also be incorporated to the device assembly 80 and/or cradle 316 to indicate to the user that the device assembly 80 is actively heating or has reached its target temperature or pressure. In yet another variation, the microprocessor or controller 110 controlling the heating of the reservoir or canister 92 can be located in the cradle 316. The reservoir or canister 92 or pressure input would have to be supplied via a direct electrical connection or a wireless connection between the cradle 316 and device assembly 80.

In yet another variation for maintaining the reservoir or canister 92 at a predetermined temperature, one or more heating elements may instead be located in the cradle 316 and used to transfer thermal energy to the reservoir or canister 92. The microprocessor or controller 110 (or an additional microprocessor) may be located in the cradle 316 in electrical communication with the one or more heating elements.

In yet another variation, the cradle 316 may be configured to both heat and cool the reservoir or canister 92. A thermoelectric unit (e.g., Peltier device) or other source of refrigeration (e.g., cooler, ice bath, etc.) may be used to cool the reservoir or canister 92 to the desired temperature range. In the case of a thermoelectric unit, such a device may be used to both cool or heat the reservoir or canister 92. In either case, the various components of the closed-loop control system could be located either in the device 80 or cradle 316 as described herein.

Figure 23:
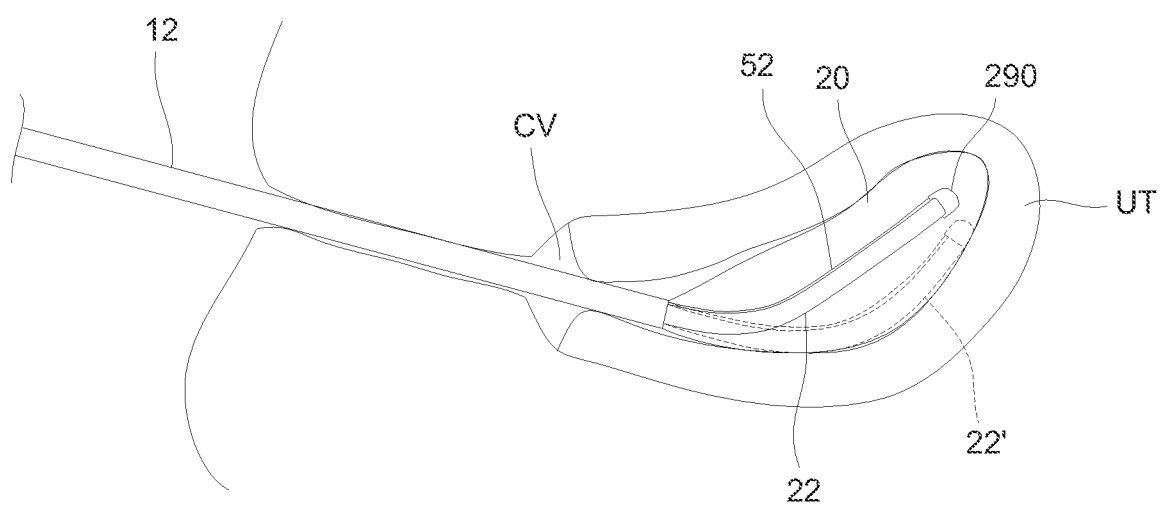
FIG. 23 shows a partial cross-sectional side view of a treatment assembly incorporating particular materials to facilitate positioning of a probe relative to the interior of a deployed liner.

While specific variations are described, it is intended that each of the features described above may be combined in any number of different combinations and such combined features are intended to be within the scope of this disclosure. For instance, the treatment assembly 80 shown in FIGS. 4A-4C may incorporate each of the features such as the reservoir or canister valve 94 and modulation control unit 96 (as shown in FIGS. 5 and 8) as well as the liquid exhaust trap 130 (as shown in FIG. 6) and exhaust collectors 150 or 160 (as shown in FIGS. 7A and 7B) into a single embodiment. The treatment assembly 80 may also incorporate the valve located within the exhaust block 46 (as shown in FIG. 9) as well as any of the liner removal variations as shown in FIGS. 10 to 18. Furthermore, the features of FIGS. 19 to 22B may also be incorporated into a single embodiment as well. The additional feature of a probe 22 or device utilizing annealed stainless steel (as shown in FIG. 23) may also be incorporated into the single embodiment as well. Additionally, any embodiment incorporating any of the various combinations may be optionally utilized with the features of a reservoir temperature control assembly and cradle 316 (as shown in FIG. 24).

While illustrative examples are described above, it will be apparent to one skilled in the art that various changes and modifications may be made therein. Moreover, various apparatus or procedures described above are also intended to be utilized in combination with one another, as practicable. The appended claims are intended to cover all such changes and modifications that fall within the true spirit and scope of the invention.

What is claimed is:
1. An inflow reservoir or canister valve, comprising:
   a valve body;
   a reservoir interface extending from the valve body and configured for fluidly coupling with a reservoir or canister containing a cryoablative agent;
   a modulation control interface defined along the body and configured for fluidly coupling to a modulation control coupler;
   a valve stem seated within a valve stem channel defined within the valve body;
   an inflow lumen defined through the valve body and extending between the reservoir interface and the modulation control interface, where the valve stem is movable between a first position which obstructs the inflow lumen and a second position which opens the inflow lumen;
   a venting lumen defined through the valve body and extending between the reservoir interface and a vent opening such that the venting lumen is in direct communication with the inflow lumen when the valve stem is in the second position;
   a vent piston which is movable between a first position which obstructs the venting lumen and a second position where the vent piston is freely translatable and which opens the venting lumen; and
   a reservoir engagement control which is coupled to the valve stem and which is rotatable about an exterior of a reservoir housing so as to rotate the valve stem to move the valve stem from its first position to its second position.

2. The valve of claim 1 further comprising a reservoir lumen insert extending from the reservoir interface.

3. The valve of claim 1 further comprising a removable locking mechanism which is positionable to obstruct movement of the vent piston.

4. The valve of claim 1 further comprising a microprocessor in electrical communication with the reservoir engagement control such that actuation of the reservoir engagement control is indicative to the microprocessor of an open reservoir or canister.

5. The valve of claim 1 further comprising a modulation control unit engaged with the modulation control interface.

6. The valve of claim 5 wherein the modulation control unit comprises an actuatable solenoid valve.

7. The valve of claim 1 further comprising a microprocessor in electrical communication with the inflow reservoir or canister valve.

8. The valve of claim 7 further comprising one or more pressure or temperature sensors in communication with the microprocessor.

9. The valve of claim 1 further comprising:
   an elongate probe having a distal tip and a flexible length;
   at least one infusion lumen positioned through or along the elongate probe and in fluid communication with the inflow lumen, wherein the infusion lumen defines one or more openings along its length; and
   a liner expandably enclosing the probe.

10. The valve of claim 9 further comprising at least one delivery lumen slidingly positioned through or along the infusion lumen, wherein the delivery lumen is configured to translate relative to the infusion lumen to control a number of unobstructed openings along the infusion lumen.

11. The valve of claim 9 further comprising an exhaust lumen in fluid communication with the elongate probe.

12. The valve of claim 11 further comprising a liquid exhaust trap in fluid communication with the exhaust lumen.

13. The valve of claim 11 further comprising an exhaust collector in fluid communication with the exhaust lumen.

14. The valve of claim 11 further comprising an actuatable valve in fluid communication with the exhaust lumen.

15. The valve of claim 9 further comprising a fluid lumen defined through an interior of the liner while fluidly isolated from the interior and where the fluid lumen is in communication with an exterior of the liner.

16. The valve of claim 9 further comprising at least one wire or tether attached to the liner, wherein the wire or tether is configured to retract the liner.

17. The valve of claim 9 further comprising an atraumatic tip attached to a distal end of the probe.

18. The valve of claim 9 further comprising a cradle which is configured to receive a handle assembly enclosing the reservoir or canister.

19. The valve of claim 1 further comprising a warming element in thermal communication with the reservoir or canister.

20. The valve of claim 1 further comprising a vent piston positioned to selectively obstruct the venting lumen when the valve stem is in the second position.

* * * * *